United States Patent
Nitta et al.

(10) Patent No.: US 10,074,197 B2
(45) Date of Patent: Sep. 11, 2018

(54) X-RAY COMPUTED TOMOGRAPHY APPARATUS, IMAGE PROCESSING APPARATUS, AND IMAGE PROCESSING METHOD

(71) Applicant: TOSHIBA MEDICAL SYSTEMS CORPORATION, Otawara-Shi (JP)

(72) Inventors: Shuhei Nitta, Ota (JP); Taichiro Shiodera, Shinagawa (JP); Tomoyuki Takeguchi, Kawasaki (JP); Hidenori Takeshima, Ebina (JP); Toshiyuki Ono, Kawasaki (JP); Takashi Ida, Kawasaki (JP); Hiroaki Nakai, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 353 days.

(21) Appl. No.: 14/842,111

(22) Filed: Sep. 1, 2015

(65) Prior Publication Data

US 2016/0058404 A1    Mar. 3, 2016

(30) Foreign Application Priority Data

Sep. 2, 2014 (JP) .................................. 2014-178450

(51) Int. Cl.
*A61B 6/03* (2006.01)
*G06T 11/00* (2006.01)
(Continued)

(52) U.S. Cl.
CPC ............ *G06T 11/005* (2013.01); *A61B 6/032* (2013.01); *A61B 6/4241* (2013.01);
(Continued)

(58) Field of Classification Search
CPC ........... A61B 6/00; A61B 6/481; A61B 6/482; G01N 23/00; G01N 2223/00; G01N 23/04;
(Continued)

(56) References Cited

U.S. PATENT DOCUMENTS

| 6,408,050 B1 * | 6/2002 | Han | ........................ G01T 1/17 378/98.11 |
| 7,801,264 B2 * | 9/2010 | Wu | ........................ A61B 6/032 378/5 |

(Continued)

FOREIGN PATENT DOCUMENTS

| JP | 05-161633 | 6/1993 |
| JP | WO 2009/131109 A1 | 10/2009 |

(Continued)

*Primary Examiner* — Thomas R Artman
(74) *Attorney, Agent, or Firm* — Oblon, McClelland, Maier & Neustadt, L.L.P.

(57) ABSTRACT

An X-ray computed-tomography (CT) apparatus of an embodiment includes an X-ray tube, an X-ray detector, and processing circuitry. The X-ray tube is configured to generate an X-ray. The X-ray detector includes a plurality of X-ray detection elements configured to output a signal based on the X-ray entered therein. The processing circuitry is configured to derive a constraint condition by using at least one piece of projection data out of a plurality of pieces of projection data corresponding energy bins of which differ at least partially, calculate an effective length that is a total length for which the X-ray has passed through a region in which a material to be decomposed is present, and generate image data showing information about the material by using the projection data and the effective length.

16 Claims, 16 Drawing Sheets

(51) Int. Cl.
    *G01N 23/046* (2018.01)
    *A61B 6/00* (2006.01)
    *G01N 23/087* (2018.01)
(52) U.S. Cl.
    CPC ............ *A61B 6/5205* (2013.01); *A61B 6/481* (2013.01); *A61B 6/482* (2013.01); *G01N 23/046* (2013.01); *G01N 23/087* (2013.01); *G06T 2211/408* (2013.01)
(58) Field of Classification Search
    CPC .. G01N 23/046; G01N 23/083; G01N 23/087; G01N 23/10; G01N 2223/40; G01N 2223/401; G01N 2223/402; G01N 2223/405; G01N 2223/419; G01N 2223/423; G01N 2223/601; G01N 2223/633; G01N 2223/639; G06T 7/0002; G06T 7/0004; G06T 11/008
    See application file for complete search history.

(56) References Cited

U.S. PATENT DOCUMENTS

| 8,442,289 | B2 | 5/2013 | Kadomura et al. | |
|---|---|---|---|---|
| 2009/0052621 | A1* | 2/2009 | Walter | A61B 5/4869 378/53 |
| 2009/0161814 | A1* | 6/2009 | Wu | A61B 6/032 378/5 |
| 2016/0058404 | A1* | 3/2016 | Nitta | A61B 6/4241 378/5 |
| 2016/0178762 | A1* | 6/2016 | Rodrigues | A61B 6/032 378/19 |
| 2016/0202364 | A1* | 7/2016 | Wang | A61B 6/032 378/5 |
| 2017/0202531 | A1* | 7/2017 | Nitta | A61B 6/5211 |

FOREIGN PATENT DOCUMENTS

| JP | 2010-253138 A | 11/2010 |
|---|---|---|
| JP | 2011-24773 A | 2/2011 |

* cited by examiner

US 10,074,197 B2

X-RAY COMPUTED TOMOGRAPHY APPARATUS, IMAGE PROCESSING APPARATUS, AND IMAGE PROCESSING METHOD

CROSS-REFERENCE TO RELATED APPLICATION

This application is based upon and claims the benefit of priority from Japanese Patent Application No. 2014-178450, filed on Sep. 2, 2014; the entire contents of which are incorporated herein by reference.

FIELD

Embodiments described herein relate generally to an X-ray computed tomography (CT) apparatus, an image processing apparatus, and an image processing method.

BACKGROUND

As application of X-ray CT, there is a technique of decomposing kinds, atomic numbers, densities, and the like of materials included in a subject based on projection data that corresponds to a plurality of energy bins, by using a fact that X-ray absorption properties differ by materials. This is called material decomposition. As the monochromaticity of a divided energy bin increases, the difference in interaction between an identified material and other materials increases. Therefore, to perform the material decomposition with high accuracy, it is preferable that an X-ray having high monochromaticity, that is, an X-ray having a narrow energy bin be used.

On the other hand, if an X-ray having a narrow energy bin or a low dose of X-ray is used to reduce the exposure dose of a subject, the number of photons decreases, and therefore, it becomes more likely to be affected by a noise. Accordingly, in the conventional material decomposition using multi-energy CT, it has been difficult to perform material decomposition with high accuracy when there is much noise due to a low dose.

DETAILED DESCRIPTION

Figure 1:
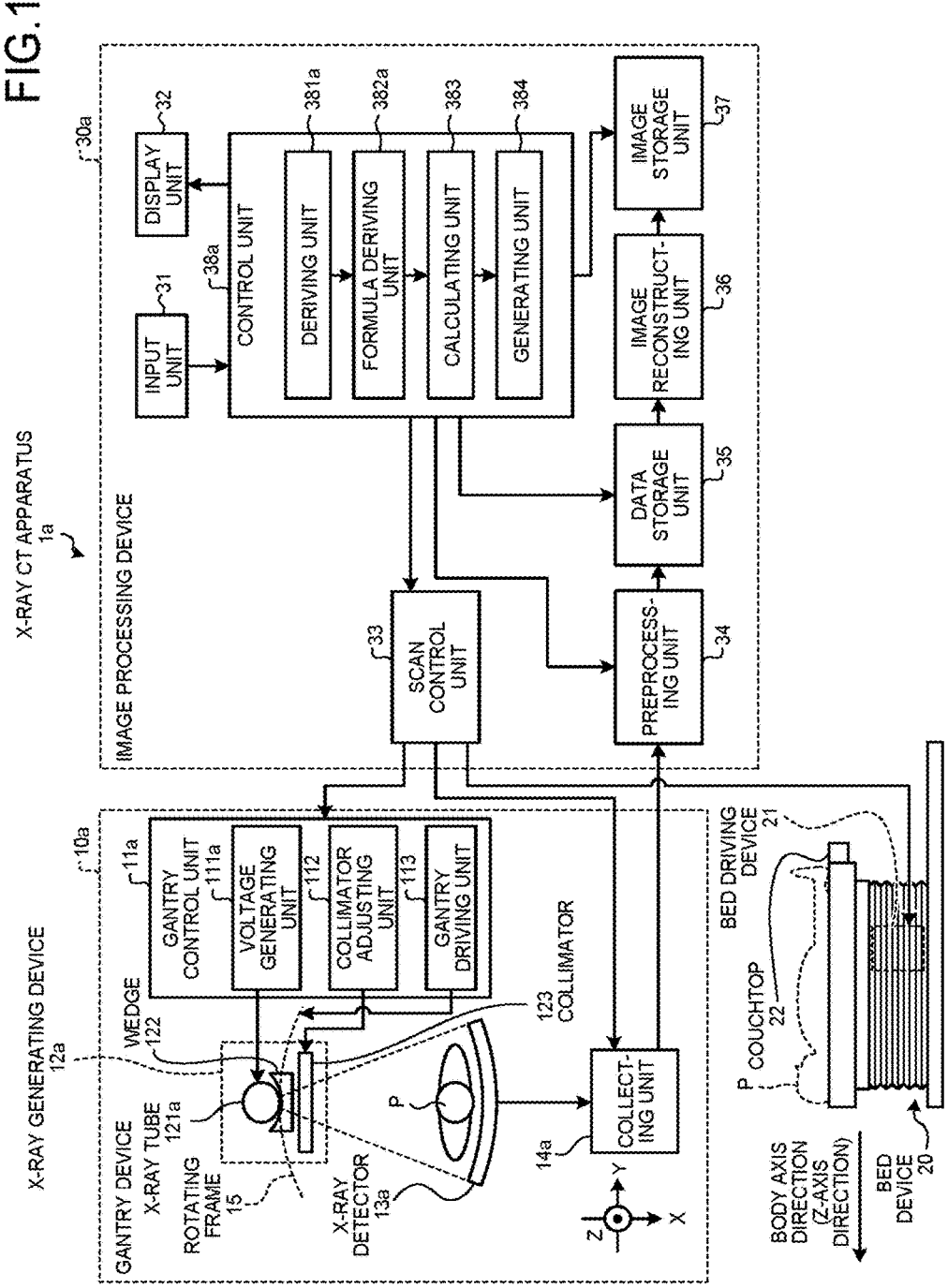
FIG. 1 depicts an X-ray CT apparatus according to some embodiments.

An X-ray computed-tomography (CT) apparatus of an embodiment includes an X-ray tube, an X-ray detector, and processing circuitry. The X-ray tube is configured to generate an X-ray. The X-ray detector includes a plurality of X-ray detection elements configured to output a signal based on the X-ray entered therein. The processing circuitry is configured to derive a constraint condition by using at least one piece of projection data out of a plurality of pieces of projection data corresponding energy bins of which differ at least partially, calculate an effective length that is a total length for which the X-ray has passed through a region in which a material to be decomposed is present, and generate image data showing information about the material by using the projection data and the effective length.

Embodiments of an X-ray CT apparatus are explained in detail below with reference to the accompanying drawings. In the following embodiments, parts referenced by same reference characters act similarly, and duplicated explanation is omitted as appropriate.

First Embodiment

Figure 2:
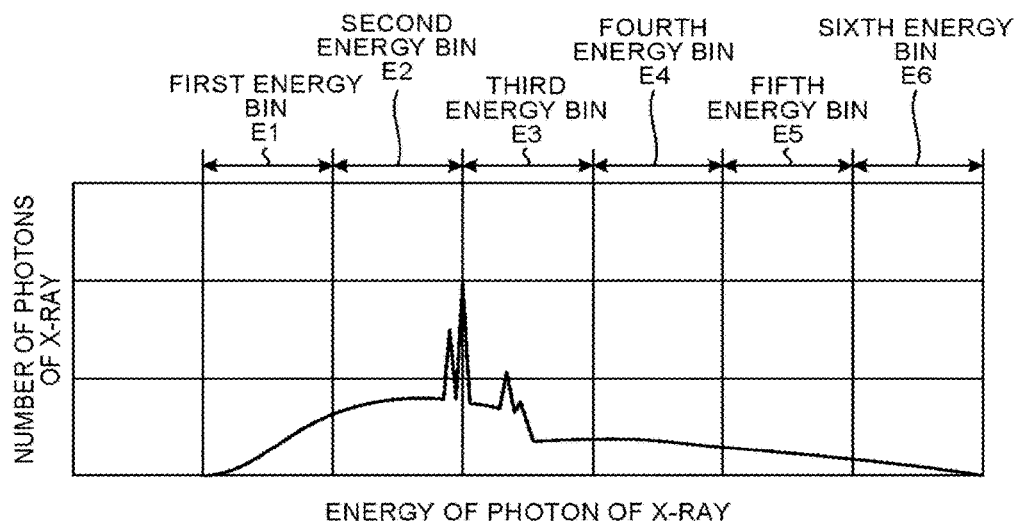
FIG. 2 depicts energy bins used in the first embodiment.

FIG. 1 depicts an X-ray CT apparatus 1a according to some embodiments. FIG. 2 depicts energy bins that are used in the first embodiment. The X-ray CT apparatus 1a includes a gantry device 10a, a bed device 20, and an image processing device 30a as shown in FIG. 1. The X-ray CT apparatus 1a according to the first embodiment is an apparatus that is enabled to perform photon-counting CT.

The gantry device 10a collects projection data described later by irradiating X-rays to a subject P. The gantry device 10a includes a gantry control unit 11a, an X-ray generating device 12a, an X-ray detector 13a, a collecting unit 14a, and a rotating frame 15.

The gantry control unit 11a controls an action of the X-ray generating device 12a and the rotating frame 15 based on control of a scan control unit 33 described later. The gantry control unit 11a includes a voltage generating unit 111a, a collimator adjusting unit 112, and a gantry driving unit 113. The voltage generating unit 111a supplies a tube voltage to an X-ray tube 121a described later. The collimator adjusting unit 112 adjusts the degree of aperture and the position of the collimator 123, to adjust an irradiation range of an X-ray that is irradiated to the subject P from the X-ray generating device 12a. For example, the collimator adjusting unit 112 adjusts the degree of aperture of the collimator 123 to adjust an irradiating range of an X-ray, that is, a fan angle and a cone angle of an X-ray. The gantry drive unit 113, by rotatively driving the rotating frame 15, rotates the X-ray generating device 12a and the X-ray detector 13a in a circular path centered on the subject P.

The X-ray generating device 12a generates an X-ray to be irradiated to the subject P. The X-ray generating device 12a includes the X-ray tube 121a, a wedge 122, and the collimator 123. The X-ray tube 121a irradiates a beam of X-ray to be irradiated to a subject by the tube voltage supplied by the voltage generating unit 111a. The X-ray tube 121a is a vacuum tube that generates an X-ray having a spreading cone-shaped or a pyramid-shaped beam along a body axis of the subject P. This beam-shaped X-ray is also called a cone beam. The X-ray tube 121a irradiates a cone beam to the subject P according to rotation of the rotating frame 15. The wedge 122 is an X-ray filter to adjust an X-ray dose of an X-ray that is irradiated from the X-ray tube 121a. The collimator 123 is a slit to narrow an irradiation range of an X-ray for which an X-ray dose is adjusted by the wedge 122, by control of the collimator adjusting unit 112.

The X-ray detector 13a is a multi-row detector that includes a plurality of X-ray detection elements that output a signal based on an incident X-ray. The X-ray detection elements are arranged in a channel direction and a slice direction. The channel direction is a direction of a circumference of the rotating frame 15, and the slice direction is a direction of a body axis of the subject P. The X-ray detection element included in the X-ray detector 13a outputs a pulse electric signal that enables to measure energy of photon and to count the number of photons, each time one photon of an X-ray enters therein. The collecting unit 14a described later can count the number of photons that have entered in the respective X-ray detection elements by counting the number of the electric signals. Moreover, the collecting unit 14a described later can measure energy of a photon that caused the output of the electric signal by performing an arithmetic processing based on a waveform of a pulse.

The X-ray detection element included in the X-ray detector 13a is, for example, a cadmium telluride (CdTe) based semiconductor element, and the X-ray detector 13a is so-called direct conversion detector. The direct conversion director is a detector that directly converts a photon that enters the X-ray detection element into an electric signal. The electric signal that is output from the X-ray detector 13a by at least one of an electron generated by entrance of a photon traveling toward a collector electrode having a positive potential, and a positive hole generated by entrance of a photon traveling toward a collector electrode having a negative potential. The X-ray detector 13a shown in FIG. 1 may be so-called an indirect conversion detector. The indirection conversion detector is a detector that converts a photon entering an X-ray detection element into a scintillator light by a scintillator, and then converts the scintillator light into an electric signal by an optical sensor such as a photomultiplier tube.

The collecting unit 14a collects counting data that is a result obtained by performing counting processing using the electric signal that is output by the X-ray detector 13a. The counting data is data in which a position (view) of the X-ray tube 121a, a position of an X-ray detection element to which a photon has entered, energy of the photon, and a counted value of photons are associated with each other. Furthermore, the collecting unit 14a distributes energy of each photon measured from the electric signal into predetermined a plurality of energy bins, and thereby collects projection data of each energy bin having a predetermined width. The counted value of photons included in the counting data may be a value per unit time (counting rate).

For example, the collecting unit 14a classifies counting data collected at respective positions of the respective X-ray detection elements and the X-ray tube 121a under energies of photons, and a counted value of photons is distributed to any one of a first energy bin E1, a second energy bin E2, a third energy bin E3, a fourth energy bin E4, a fifth energy bin E5, and a sixth energy bin E6 shown in FIG. 2. Thus, the collecting unit 14a generates projection data that corresponds to each of the first energy bin E1, the second energy bin E2, the third energy bin E3, the fourth energy bin E4, the fifth energy bin E5, and the sixth energy bin E6. Moreover, the collecting unit 14a generates projection data in which counting values of photons of at least two pieces of projection data out of these a plurality of pieces of projection data are added up at respective positions of the respective X-ray detection elements and the X-ray tube 121a. For example, the collecting unit 14a collects six kinds of projection data having different energy bins for each view, and generates projection data in which counted values of photons of these six kinds of projection data are added up at respective positions of the X-ray tube 121a and the respective X-ray detection elements. In the explanation of the first embodiment, projection data in which counted values of photons of the projection data of a plurality of energy bins in the respective positions of the X-ray tube 121a and the respective X-ray detection elements are totalized is defined as first projection data, and each projection data before totalizing the counted values of photons of projection data of a plurality of energy bins is defined as second projection data. Because the first projection data is data in which the counted values of photons of these six pieces of second projection data, the number of photons of an X-ray is large, and noises are few. That is, the energy bins corresponding to the first projection data differ from energy bins that are used in material decomposition processing. Moreover, the first projection data uses projection data of all of the energy bins shown in FIG. 2. The first projection data may be projection data in which the counted values of photons of two to five pieces of the second projection data as long as an influence of a noise can be reduced. For example, the first projection data can be projection data in which the counted values of photons in the second projection data of the first energy bin E1, the second energy bin E2, the third energy bin E3, and the fourth energy bin E4 are added up.

FIG. 2 depicts one example in which the first energy bin E1, the second energy bin E2, the third energy bin E3, the fourth energy bin E4, the fifth energy bin E5, and the sixth energy bin E6 having the same energy width are set in an energy distribution of an X-ray that is irradiated to the subject P from the X-ray tube 121a. As shown in FIG. 2, in the first embodiment, a range in which all energy bins corresponding to projection data used when a constraint condition is derived by a deriving unit 381a described later is larger than a range in which all energy bins corresponding to projection data used when an effective length is calculated by a calculating unit 383 described later.

A method of setting energy bins in an energy distribution of an X-ray that is irradiated to the subject P is not limited to the one shown in FIG. 2. The number of energy bins, the width of energy bins, and the like can be determined arbitrarily. Two or more energy bins may be partially overlapped. Furthermore, if energy bins are set on both sides sandwiching a K-absorption edge of a material to be decomposed, X-ray attenuation coefficient values significantly differ from each other on the both sides of the K-absorption edge, and therefore, it is preferable in performing material decomposition. Moreover, if energy bins are set such that sharp contrast is obtained according to a material to be decomposed, material decomposition can be performed with higher accuracy. For example, a hard tissue, such as a bone, is more likely to allow an X-ray having high energy to pass therethrough than an X-ray having low energy. Therefore, if energy of energy bins is set high, the contrast is like to be sharp. On the contrary, a soft tissue, such as a cartilage, is likely to allow an X-ray having low energy to pass therethrough than an X-ray having high energy. Therefore, if energy of energy bins is set low, the contrast is likely to be sharp. The X-ray CT apparatus 1a according to the first embodiment is configured such that setting of energy bins can be arbitrarily changed by an operator, for example. Furthermore, for example, a control unit 38a described later controls distribution of counted values of photons performed by the collecting unit 14a by informing setting information of energy bins to the gantry device 10a. In the first embodiment, generation of the first projection data may be performed by the image processing device 30a.

The collecting unit 14a transmits collected projection data to the image processing device 30a. For example, the collecting unit 14a transmits projection data of respective views collectively in a data format of sinogram. The sinogram is data in which signals detected by the X-ray detector 13a at respective positions (respective views) of the X-ray tube 121a are aligned. The sinogram is data in which signals (counted values in the present embodiment) detected by the X-ray detector 13a are allocated in a two-dimensional rectangular coordinate system a first direction of which is a view direction indicating a position of the X-ray tube 121a and a second direction of which is a channel direction of the X-ray detector 13a perpendicular to the first direction. The collecting unit 14a generates a sinogram per line in the slice direction. In the following, explanation is given with an example in which projection data is a sinogram. The collecting unit 14a is also called a data acquisition system (DAS).

The rotating frame 15 is an annular frame that supports the X-ray generating device 12a and the X-ray detector 13a so as to be opposed to each other about the subject P. The rotating frame 15 is driven by the gantry driving unit 113, and rotates on a circular orbit about the subject P in center at a high speed.

The bed device 20 includes a bed driving device 21 and a couchtop 22, and the subject P is placed. The bed driving device 21 moves the subject P inside the rotating frame 15 by moving the couchtop 22 on which the subject P is placed in a Z-axis direction based on control by the scan control unit 33 described later. The gantry device 10a performs, for example, a helical scan in which the subject P is helically scanned by rotating the rotating frame 15 while moving the couchtop 22. Alternatively, the gantry device 10a performs a conventional scan in which the subject P is scanned in a circular orbit by rotating the rotating frame 15 after the couchtop 22 is moved, while the position of the subject P is fixed. Alternatively, the gantry device 10a performs a step-and-shoot scan in which the conventional scan is performed in a plurality of scan areas while moving the couchtop 22 at regular intervals.

The image processing device 30a accepts an operation of the X-ray CT apparatus 1a by an operator, and performs various kinds of image processing such as reconstruction processing of a CT image using projection data collected by the gantry device 10a. The image processing device 30a includes an input unit 31, a display unit 32, the scan control unit 33, a preprocessing unit 34, a data storage unit 35, an image reconstructing unit 36, an image storage unit 37, and a control unit 38a.

The input unit 31 is a mouse, a keyboard, and the like that are used by an operator of the X-ray CT apparatus 1a to input various kinds of instructions and various kinds of settings, and transfers information about an instruction and a setting accepted from an operator to the control unit 38a. The display unit 32 is a monitor that is referred to by an operator. On the display unit 32, a CT image, a display image described later, a graphical user interface (GUI) to accept various kinds of settings from an operator through the input unit 31, and the like are displayed. Moreover, the input unit 31 is used to select a constraint condition described later.

The scan control unit 33 controls actions of the gantry control unit 11a, the collecting unit 14a, and the bed driving device 21 based on control of the control unit 38a. Specifically, the scan control unit 33 causes the rotating frame 15 to rotate, causes the X-ray tube 121a to emit an X-ray, and adjusts the degree of aperture and the position of the collimator 123 at the time of performing photon-counting CT imaging, by controlling the gantry control unit 11a. Furthermore, the scan control unit 33 controls the collecting unit 14a based on control of the control unit 38a. Moreover the scan control unit 33 causes the couchtop 22 to move by controlling the bed driving device 21 based on control of the control unit 38a, at the time of imaging the subject P.

The preprocessing unit 34 performs correction processing such as logarithmic conversion, offset correction, sensitivity correction, beam hardening correction, scatter correction, and the like on projection data generated by the collecting unit 14a, to store in the data storage unit 35. The projection data that is subjected to correction processing by the preprocessing unit 34 is also called raw data.

The data storage unit 35 stores raw data, that is, projection data subjected to correction processing by the preprocessing unit 34. In the following, raw data is described as projection data in some cases, for simplicity of explanation.

The image reconstructing unit 36 reconstructs projection data stored in the data storage unit 35, to generate a CT image. As for a reconstruction method, there are various methods and, for example, back projection processing is one. Moreover, as the back projection processing, for example, a filtered back projection (FBP) is applicable. The image reconstructing unit 36 may perform reconstruction processing, for example, by successive approximation. The image reconstructing unit 36 stores a generated CT image in the image storage unit 37.

The image storage unit 37 stores a CT image reconstructed by the image reconstructing unit 36 and a display image described later. For example, in the first embodiment, the image reconstructing unit 36 generates a CT image using projection data that is stored in the data storage unit 35 as the first projection image, and stores the CT image in the image storage unit 37.

The control unit 38a controls the X-ray CT apparatus 1a by controlling actions of the gantry device 10a, the bed device 20, and the image processing device 30a. The control unit 38a controls the scan control unit 33 to perform a scan, and collects projection data from the gantry device 10a. The control unit 38a controls the preprocessing unit 34 to perform the correction processing described above on the projection data. The control unit 38a controls the display unit 32 to display projection data stored in the data storage unit 35 or image data stored in the image storage unit 37.

The data storage unit 35 and the image storage unit 37 described above can be implemented by a random access memory (RAM), a semiconductor memory device such as a flash memory, a hard disk, an optical disk, and the like. Moreover, the scan control unit 33, the preprocessing unit 34, the image reconstructing unit 36, and the control unit 38a described above can be implemented by an integrated circuit such as an application specific integrated circuit (ASIC) and a field programmable gate array (FPGA), or an electronic circuit such as a central processing unit (CPU) and a micro processing unit (MPU).

The control unit 38a according to the first embodiment includes the deriving unit 381a, a formula deriving unit 382a, a calculating unit 383, and a generating unit 384.

The deriving unit 381a derives a constraint condition using at least one of a plurality of projection data each of which corresponds to energy bin of which differs at least partially. Specifically, the deriving unit 381a generates a binarized image from a CT image that is obtained by reconstructing projection data by binarization using a threshold set according to a material to be decomposed, and derives a constraint condition using projection information that is obtained by subjecting the binarized image to projection processing. Moreover, the deriving unit 381a may generate a plurality of binarized images from CT images obtained by reconstructing projection data by binarization using a plurality of thresholds set according to materials to be decomposed, and may derive a plurality of constraint conditions using a plurality of projection information obtained by subjecting the a plurality of binarized images to the projection processing. The formula deriving unit 382a derives a calculation formula to calculate an effective length of a material to be decomposed from the second projection data. The effective length of a material to be decomposed signifies a total length for which a X-ray that has been emitted from the X-ray tube 121a, passed through the subject P, and entered in the X-ray detection element included in the X-ray detector 13a has passed through a region in which the material to be decomposed is present. The calculating unit 383 calculates the effective length of a material to be decomposed using the projection data and the constraint condition. The generating unit 384 generates image data showing information about a material by using the projection data and the effective length. Furthermore, the formula deriving unit 382a may be included in the deriving unit 381a.

Figure 3:
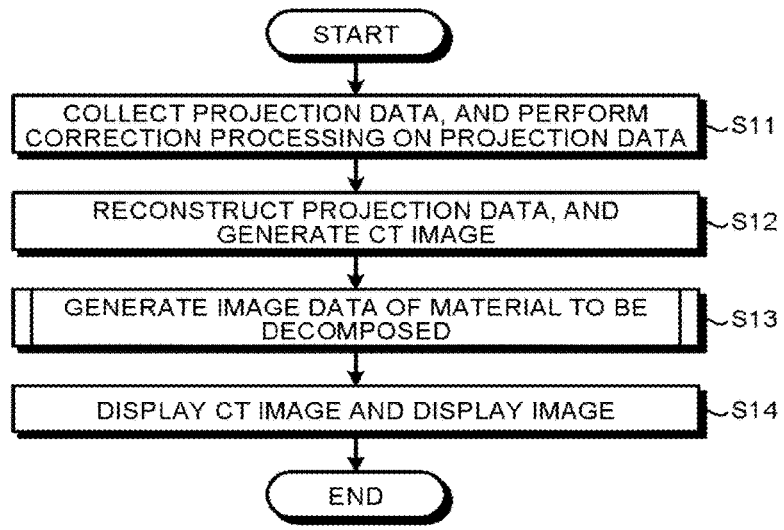
FIG. 3 is a flowchart indicating a procedure of material decomposition that is performed by the X-ray CT apparatus according to the first embodiment.
Figure 4:
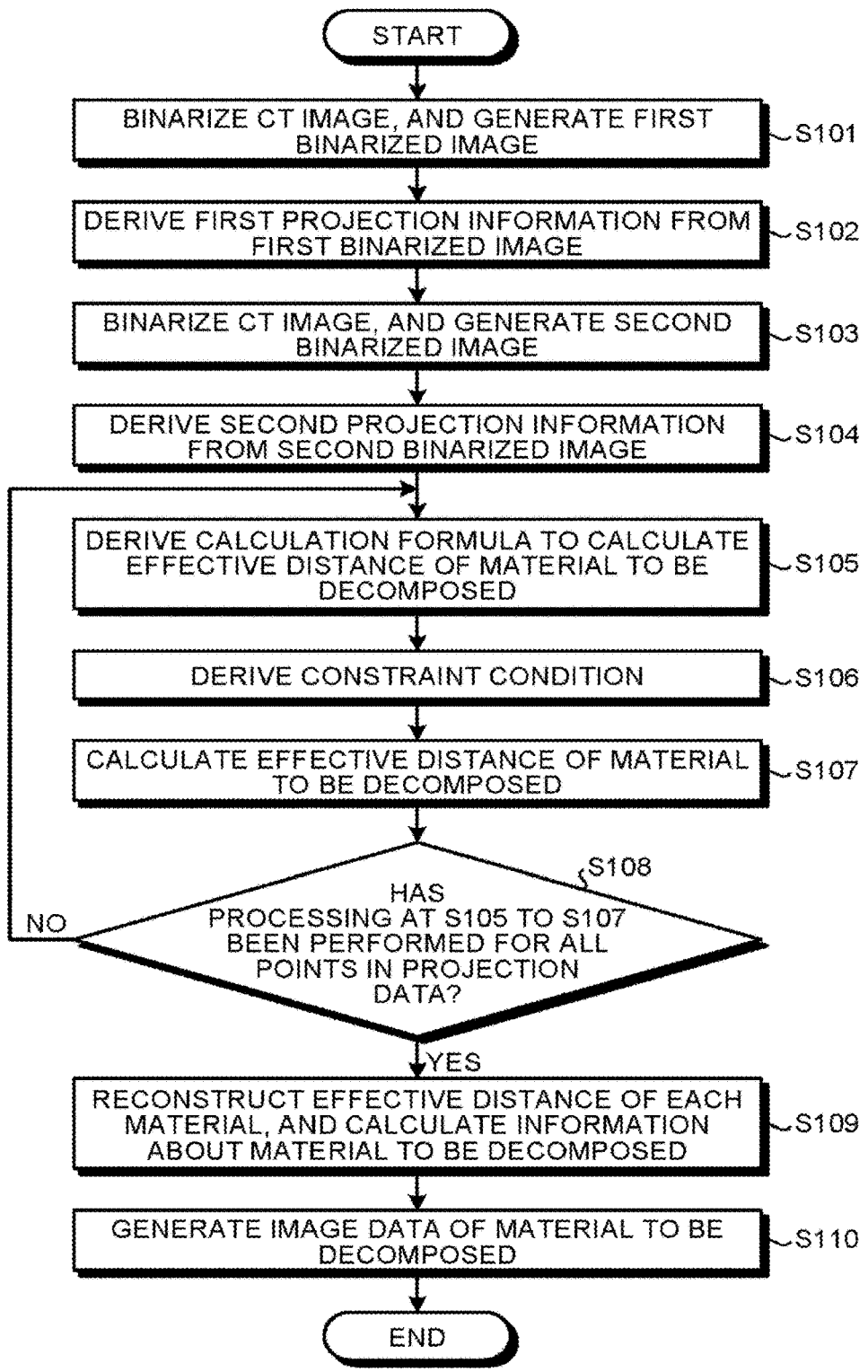
FIG. 4 is a flowchart indicating a procedure at step S13 in FIG. 3.
Figure 5:
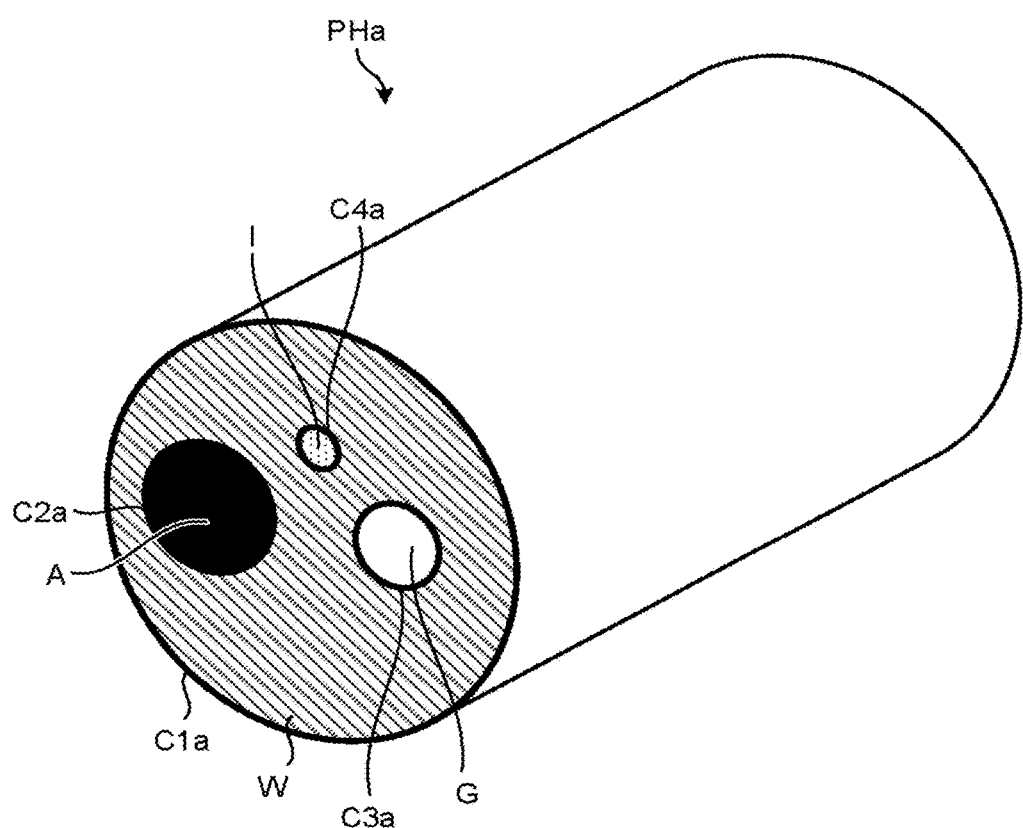
FIG. 5 depicts a phantom for which photon-counting CT is performed by the X-ray CT apparatus according to the first embodiment.
Figure 6:
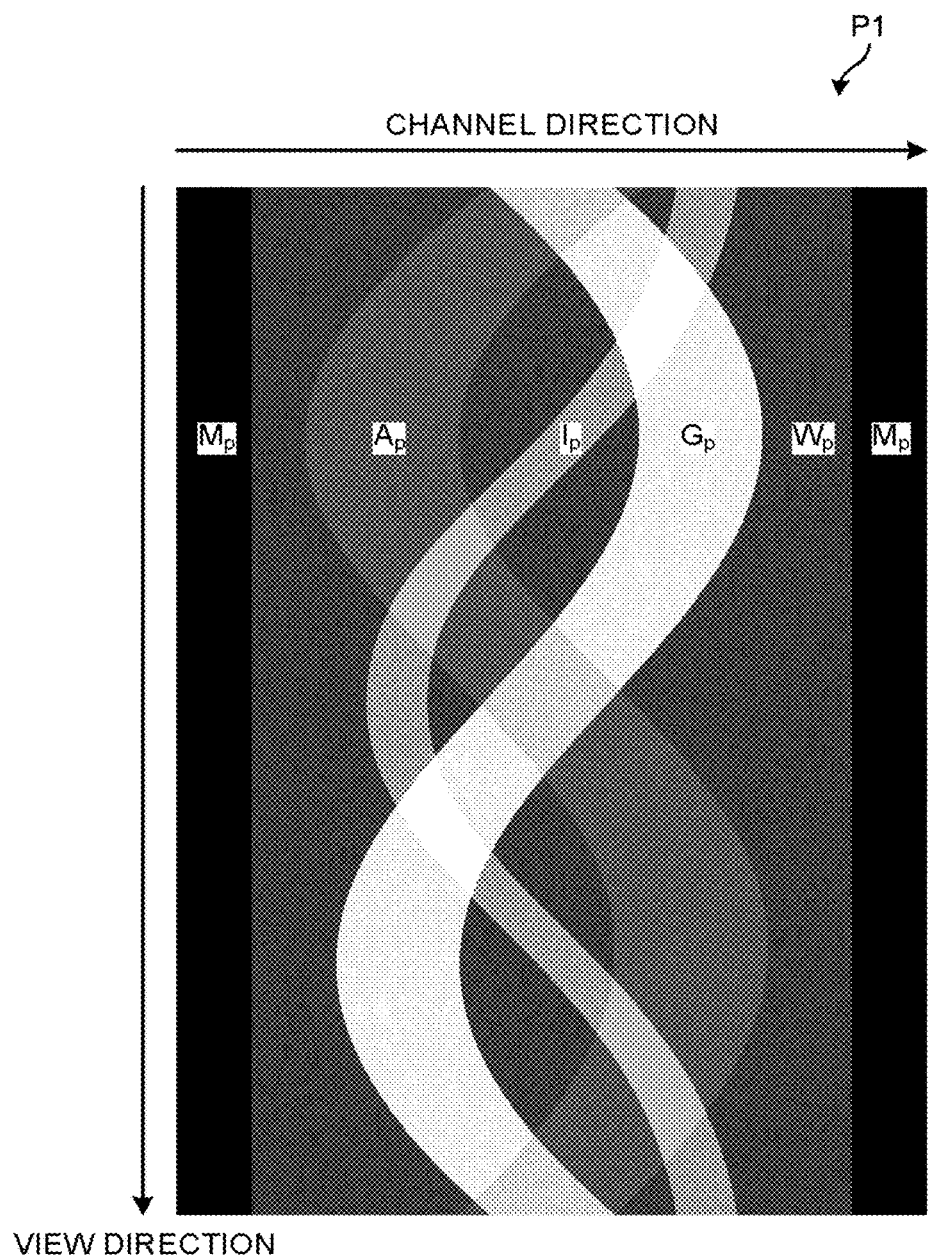
FIG. 6 depicts first projection data.
Figure 7:
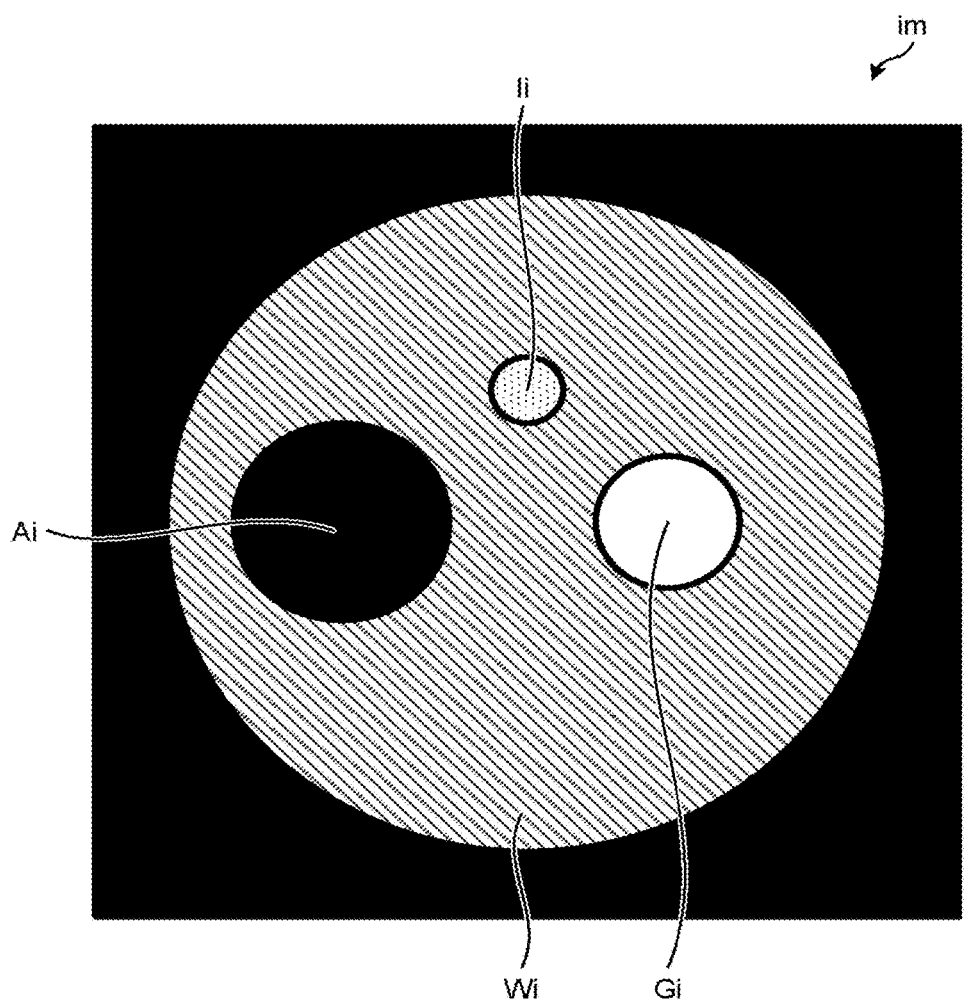
FIG. 7 depicts a CT image that is generated by reconstructing the first projection data.
Figure 8:
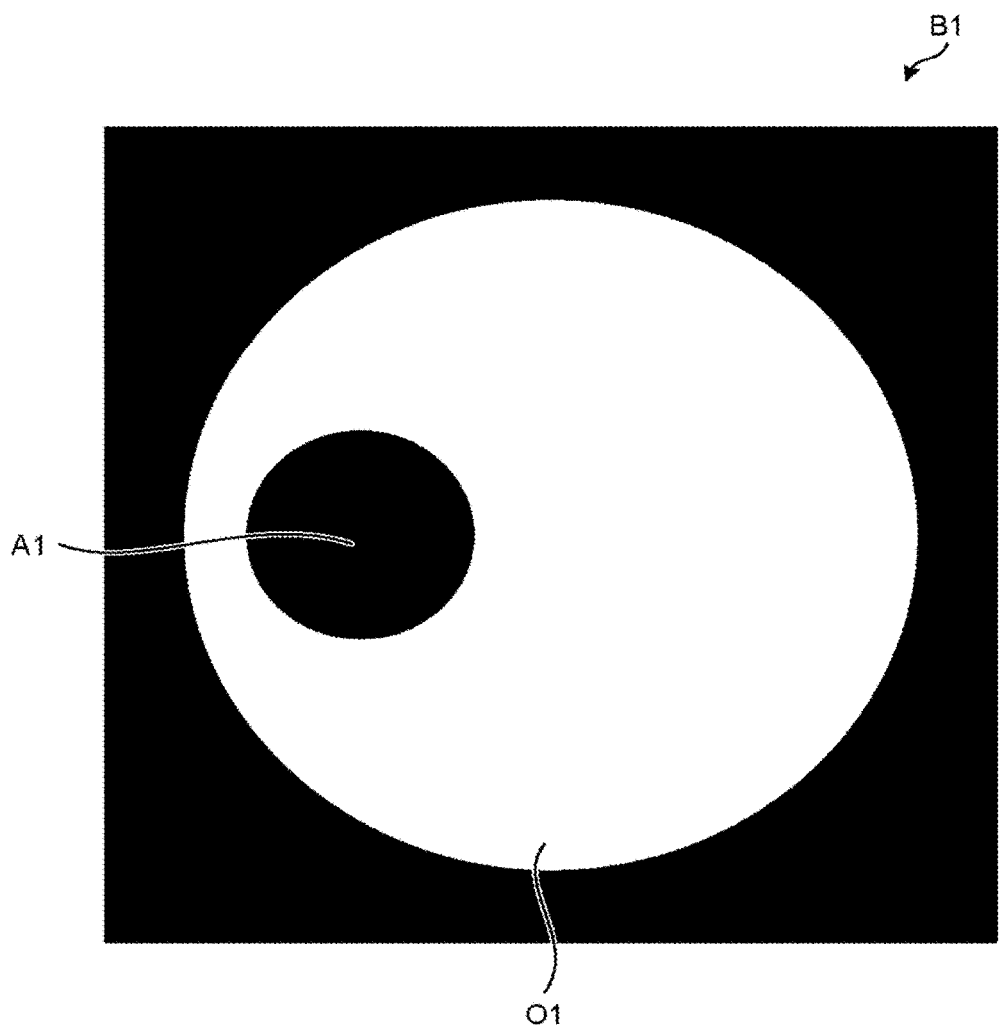
FIG. 8 depicts a first binarized image.
Figure 9:
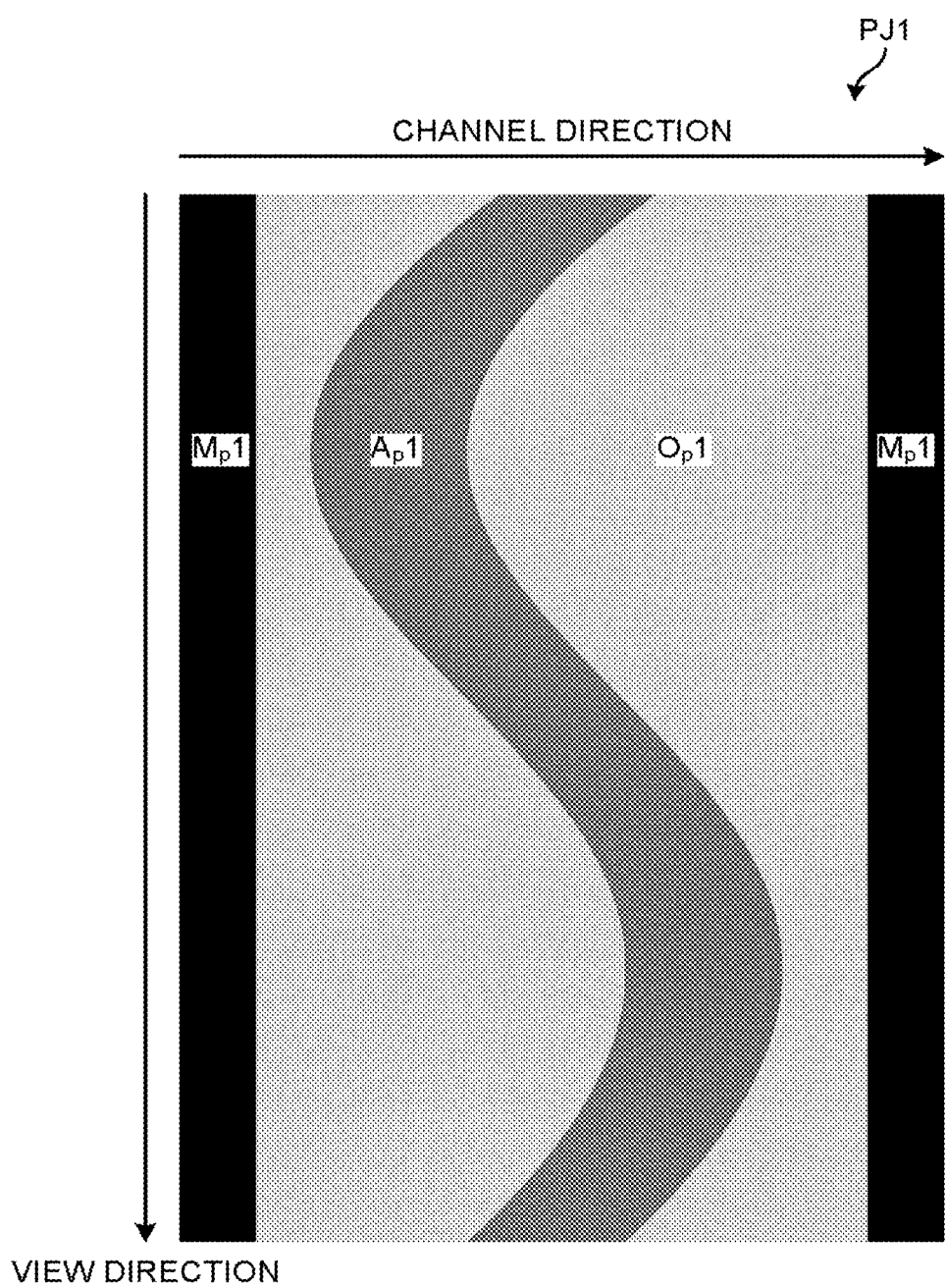
FIG. 9 depicts a first projection information derived from the first binarized image.
Figure 10:
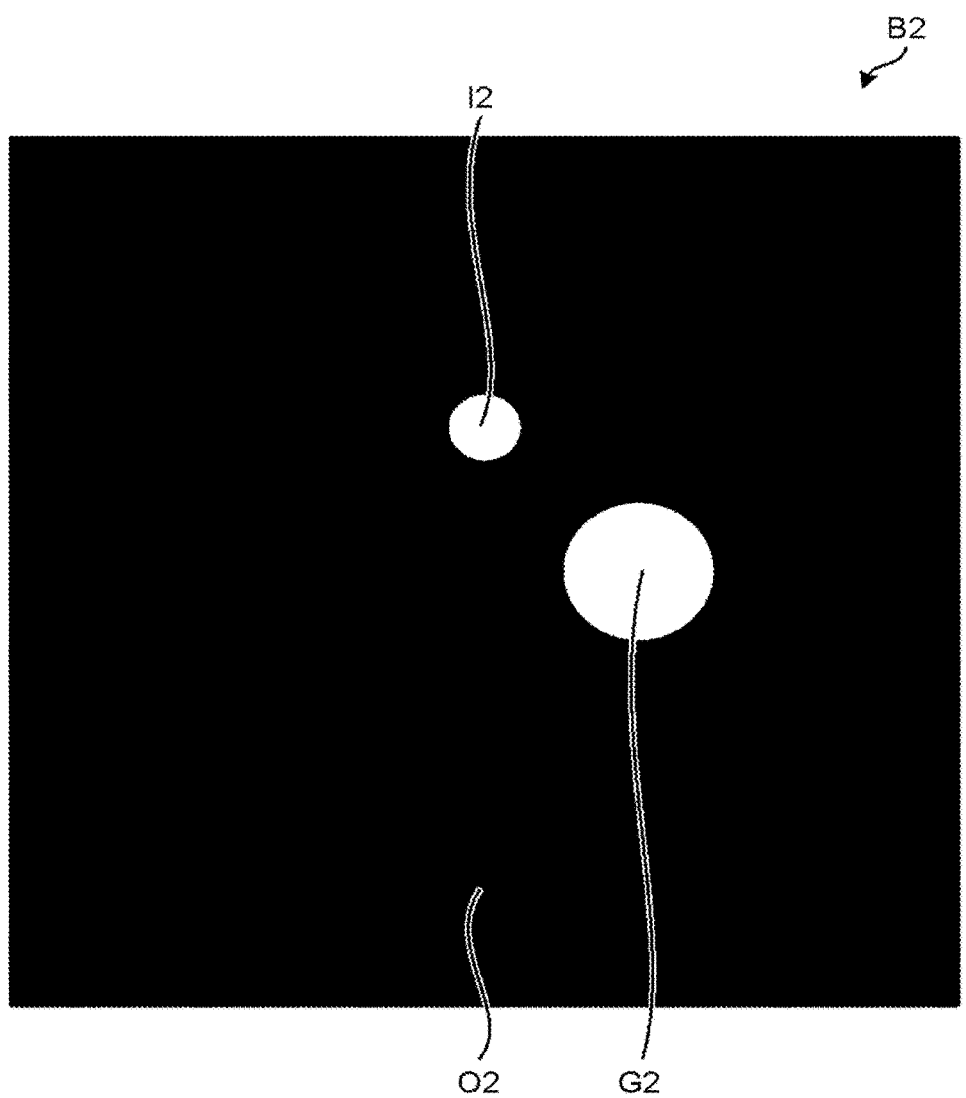
FIG. 10 depicts a second binarized image.
Figure 11:
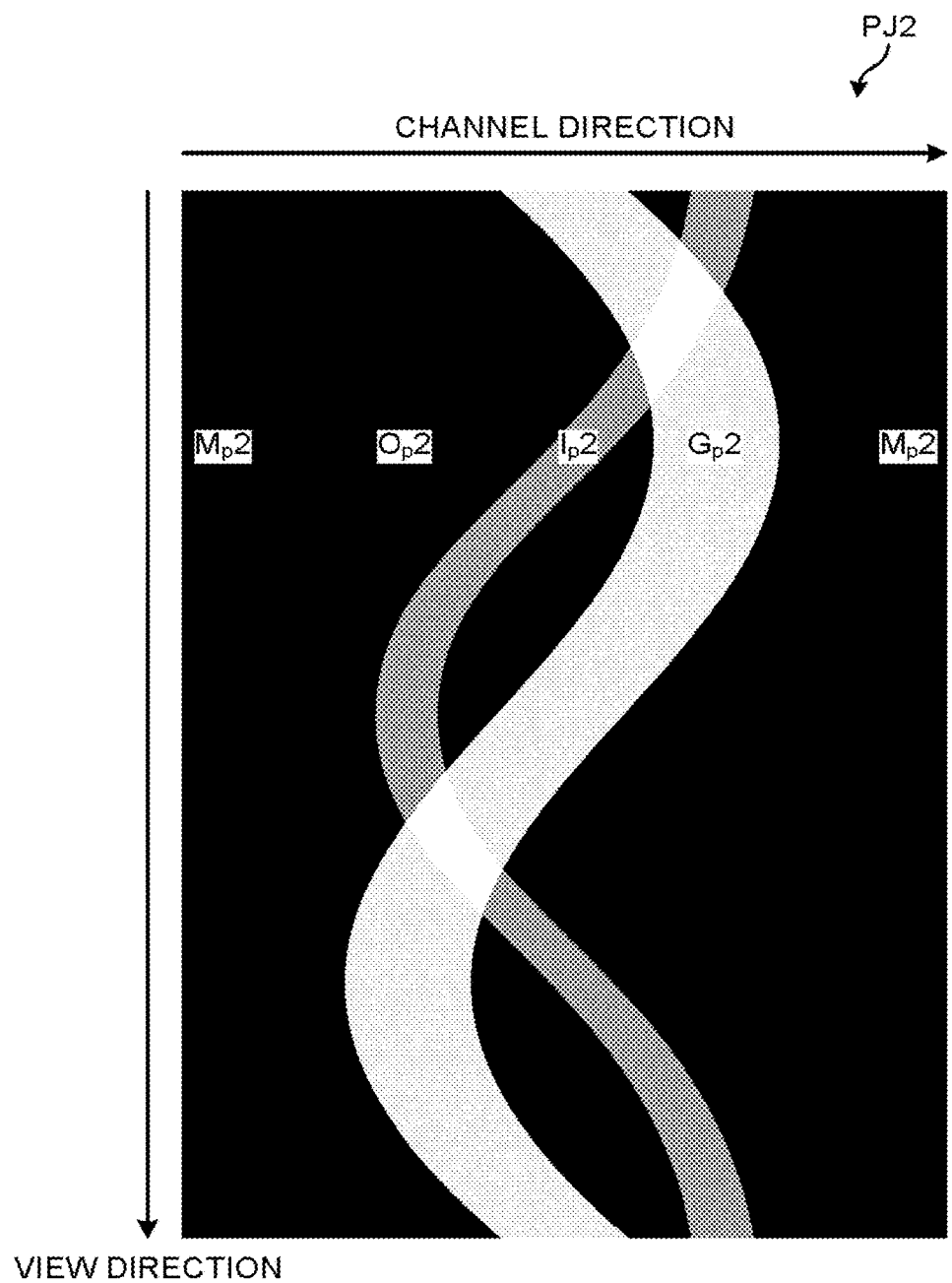
FIG. 11 depicts a second projection information derived from the second binarized image.

In the following, one example of processing performed by the deriving unit 381a, the formula deriving unit 382a, the calculating unit 383, and the generating unit 384 is explained in detail referring to FIG. 3 to FIG. 11. FIG. 3 is a flowchart indicating a procedure of material decomposition that is performed by the X-ray CT apparatus 1a according to the first embodiment. FIG. 4 is a flowchart indicating a procedure at step S13 in FIG. 3. FIG. 5 depicts a phantom PHa for which photon-counting CT is performed by the X-ray CT apparatus 1a according to the first embodiment. FIG. 6 depicts first projection data P1. FIG. 7 depicts a CT image im that is generated by reconstructing the first projection data P1. FIG. 8 depicts a first binarized image B1. FIG. 9 depicts a first projection information PJ1 derived from the first binarized image B1. FIG. 10 depicts a second binarized image B2. FIG. 11 depicts a second projection information PJ2 derived from the second binarized image B2.

In the following explanation, a case in which photon-counting CT imaging is performed with the Phantom PHa shown in FIG. 5 as the subject P is explained as an example. The phantom PHa has a cylinder C1a, a cylinder C2a, a cylinder C3a, and a cylinder C4a center axes of which are parallel to each other, and diameters of bottom surfaces of which are different from each other. The diameter of the cylinder C1a is larger than the diameters of the cylinder C2a, the cylinder C3a, and the cylinder C4a. The cylinder C2a, the cylinder C3a, and the cylinder C4a are included inside the cylinder C1a. Air A is filled inside the cylinder C2a. A gadolinium contrast agent G is filled inside the cylinder C3a. An iodine contrast agent I is filled inside the cylinder C4a. Water W is filled in a region surrounded by the cylinder C2a, the cylinder C3a, and the cylinder C4a, and the cylinder C1a. Moreover, the phantom PHa is arranged in the air.

The control unit 38a controls the gantry device 10a, the bed device 20, and the image processing device 30a to perform photon-counting CT imaging and collect projection data, and controls the preprocessing unit 34 to perform the correction processing described above on the projection data (step S11). At step S11, the correction processing is performed on the first projection data, and the second projection data of respective energy bins. FIG. 6 depicts a sinogram of the first projection data P1 that is projection data including information of all of the energy bins. In FIG. 6, a vertical direction corresponds to the view direction, and a horizontal direction corresponds to the channel direction.

As shown in FIG. 6, the first projection data P1 includes regions Mp, a region Ap, a region Ip, a region Gp and a region Wp. The regions Mp are rectangular regions that are positioned at both ends of the first projection data P1 in the channel direction, and that are long in the view direction. The region Ap, the region Ip, and the region Gp are belt-like regions meandering along the view direction. The region Wp is a region other than the region Ap, the region Ip, the region Gp, and the region Mp in the first projection data P1. At each point in the region Mp, information about the counted value of photons of an X-ray that has passed through the air not through the phantom Pha is included. At each point in the region Ap, information about the counted value of photons of an X-ray that has passed at least through the air A inside the cylinder C2a is included. At each point in the region Ip, information about the counted value of photons of an X-ray that has passed at least through an iodine contrast agent I is included. At each point in the region Gp, information about the counted value of photons of an X-ray that has passed at least through a gadolinium contrast agent G is included. At each point in the region Wp, information about the counted value of photons of an X-ray that has passed only through the water W is included.

The image reconstructing unit 36 generates a CT image im shown in FIG. 7 by reconstructing the first projection data P1 stored in the data storage unit 35 (step S12). As shown in FIG. 7, a region Wi corresponding to the water W, a region Ai corresponding to the air A, a region Ii corresponding to the iodine contrast agent I, and a region Gi corresponding to the gadolinium contrast agent G appear in the CT image im. The control unit 38a performs various kinds of processing on the CT image im generated at step S12, and generates image data of a material to be decomposed (step S13). The display unit 32 displays the CT image im and a display image (step S14). The display image signifies an image that displays information about the material to be decomposed. The information about the material to be decomposed includes a kind, an atomic number, density, and the like. Details of step S13 are as described below.

The deriving unit 381a binarizes the CT image im, to generate the first binarized image B1 shown in FIG. 8 (step S101). The first binarized image B1 is an image that is divided into a region A1 in which the air A is present and a region O1 in which the air A is not present. The region A1 in the first binarized image B1 corresponds to the region Ai in the CT image im. The region O1 in the first binarized image B1 corresponds to a combined region of the region Wi, the region Ii, and the region Gi in the CT image im. Because the X-ray attenuation coefficient of the air A is smaller than the X-ray attenuation coefficient of other materials, a difference between the brightness of the region Ai in which the air A is present and the brightness of the region other than the air A (the region Wi, the region Ii, and the region Gi) is large. Therefore, the deriving unit 381a can divide the CT image im into a high-brightness region in which a brightness value of a pixel the brightness values of which is equal to or larger than a threshold is 1, that is the region A1, and a low-brightness region in which a brightness value of a pixel the brightness value of which is smaller than the threshold is 0, that is the region O1, easily by binarization using a threshold set according to the air. Therefore, the deriving unit 381a can generate the first binarized image B1 easily from the CT image im.

The deriving unit 381a derives the first projection information PJ1 shown in FIG. 9 from the first binarized image B1 (step S102). The deriving unit 381a performs, on the first binarized image B1 that is divided into the region of the air and the region other than the air, projection processing based on information of a geometrical arrangement of the X-ray tube 121a and the X-ray detector 13a and a direction of projection (view direction), to calculate a mean-value projection image of a result of region division, thereby driving the first projection information PJ1. The first projection information PJ1 is to be information enabling to acquire a total transmission length of the region other than the air. For example, the deriving unit 381a derives the first projection information PJ1 in a data format of sinogram as shown in FIG. 9, similarly to the first projection data P1.

The brightness at each point of the first projection information PJ1 includes information about a total transmission length. The total transmission length is a total length for which an X-ray that has been emitted from the X-ray tube 121a, passed through the subject P, and entered into the X-ray detection element has passed through the region in which the air A is not present. As shown in FIG. 9, the first projection information PJ1 includes regions Mp1, a region Ap1, and a region Op1. The regions Mp1 are rectangular regions that are positioned at both ends of the first projection information PJ1 in the channel direction and that are long in the view direction. The region Ap1 is a belt-like region meandering along the view direction. The region Op1 is a region other than the region Mp1 and the region Ap1 in the first projection information PJ1.

The brightness of each point in the region Ap1 includes information about a total transmission length of an X-ray that has passed through the air A inside the cylinder C2a. The brightness of each point in the region Op1 includes information about a total transmission length of an X-ray that has not passed through the air A inside the cylinder C2a.

However, the brightness of each point in the first projection information PJ1 does not include information about a total length for which an X-ray has transmitted through the water W, a total length for which an X-ray has transmitted through the iodine contrast agent I, and a total length for which an X-ray has passed through the gadolinium contrast agent G. This is because the first projection information PJ1 is generated from the first binarized image B1 in which the region Wi with presence of the water W, the region Ii with presence of the iodine contrast agent I, and the region Gi with presence of the gadolinium contrast agent G are not distinguished. The total transmission length is used for a first constraint condition described later.

The deriving unit 381a binarizes the CT image im, to generate the second binarized image B2 shown in FIG. 10 (step S103). The second binarized image B2 is an image that is divided into a combined region of a region I2 with presence of the iodine contrast agent I and a region G2 with presence of the gadolinium contrast agent G, and a region O2 other than that. The region I2 in the second binarized image B2 corresponds to the region Ii in the CT image im. The region G2 in the second binarized image B2 corresponds to the region Gi in the CT image im. The region O2 in the second binarized image B2 corresponds to the combined region of the region Ai and the region Wi in the CT image im. Because the X-ray attenuation coefficients of the iodine contrast agent I and the gadolinium contrast agent G are larger than the X-ray attenuation coefficient of the water W and the air A, a difference between the brightness of the combined region of the region Ii in which the iodine contrast agent I is present and the region Gi in which the gadolinium contrast agent G is present and the brightness of the other region, that is, the combined region of the region Wi in which the water W is present and the region Ai in which the air A is present, is large. Accordingly, the deriving unit 381a can divide the CT image im into a high-brightness region in which a brightness value is 1, that is, the region I2 and the region G2, and a low-brightness region in which a brightness value is 0, that is, the region O2, easily by binarization using a threshold set according to a material to be decomposed. Therefore, the deriving unit 381a can generate the second binarized image B2 easily from the CT image im.

The deriving unit 381a derives the second projection information PJ2 shown in FIG. 11 from the second binarized image B2 (step S104). The second projection information PJ2 is acquired by projection processing similar to the processing performed to acquire the first projection information PJ1. For example, the deriving unit 381a derives the second projection information PJ2 in a data format of sinogram, as shown in FIG. 11.

The brightness of each point of the second projection information PJ2 includes information about an effective length of the iodine contrast agent I and an effective length of the gadolinium contrast agent G. As shown in FIG. 11, the second projection information PJ2 includes regions Mp2, a region Ip2, a region Gp2, and a region Op2. The regions Mp2 are rectangular regions that are positioned at both ends of the second projection information PJ2 in the channel direction, and are long in the view direction. The region Ip2 and the region Gp2 are belt-like regions meandering along the view direction. The region Op2 is a region other than the regions Mp2, the region Ip2, and the region Gp2 in the second projection information PJ2.

The brightness of each point in the region Ip2 includes information about at least one of an effective length of the iodine contrast agent I and an effective length of the gadolinium contrast agent G of an X-ray that has passed through the iodine contrast agent I. The brightness of each point in the region Gp2 includes information about at least an effective length of the iodine contrast agent I and an effective length of the gadolinium contrast agent G of an X-ray that has passed through the gadolinium contrast agent G. The brightness of each point in the region Op2 includes information about an effective length of the iodine contrast agent I and an effective length of the gadolinium contrast agent G of an X-ray that has not passed through the iodine contrast agent I and the gadolinium contrast agent G. Note that the information available from the second projection information PJ2 is information about a total length of the effective length of the iodine contrast agent I and the effective length of the gadolinium contrast agent G, and the effective length of the iodine contrast agent I and the effective length of the gadolinium contrast agent G are not separately available. The brightness of each point of the second projection information PJ2 expresses a presence probability of the iodine contrast agent I and the gadolinium contrast agent G. The presence probability is used for the second constraint condition described later.

Furthermore, the brightness at each point of the second projection information PJ2 does not include information about an effective length of the air A and an effective length of the water W. This is because the second projection information PJ2 is generated from the second binarized image B2 in which the region Wi with presence of the water W and the region Ai with presence of the air A are not distinguished.

The deriving unit 381a may display the first binarized image B1 and the second binarized image B2 near corresponding display images on the display unit 32. The display image is an image displaying a result of material decomposition, and is generated based on image data of the material to be decomposed. Thus, an operator of the X-ray CT apparatus 1a or an X-ray CT apparatus 1b can view a method by which the effective length of the decomposed material is calculated, and can change appropriately the method of calculating the effective length as necessary.

Moreover, it may be configured such that the deriving unit 381a displays the first projection information PJ1 and the second projection information PJ2 on the display unit 32, and an operator chooses either of the first projection information PJ1 and the second projection information PJ2 use when material decomposition is to be performed. Alternatively, it may be configured such that the first projection information PJ1 or the second projection information PJ2 is selected automatically based on an electric patient charts or imaging conditions. Thus, material decomposition can be performed according to needs of an operator, a diagnosis, an imaging condition, and the like.

Furthermore, it may be configured such that the operator corrects the first binarized image B1 and the second binarized image B2 through the input unit 31, the deriving unit 381a generates the first projection information and the second projection information again, to perform material decomposition described later. Thus, material decomposition according to needs of an operator can be performed.

The formula deriving unit 382a derives a calculation formula to calculate an effective length of a material to be decomposed (step S105). First, a method of calculating an effective length of a material to be decomposed in a conventional technique is explained. Generally, defining the number of photons of an X-ray irradiated to the subject P as Co, the number of photons of an X-ray detected by the X-ray detection element as C, energy of an X-ray as E, energy of an X-ray in the n-th energy bin (n=1, 2, . . . , 6) as $E_n$, the number of materials to be decomposed as m, an X-ray attenuation coefficient of a material to be decomposed as $\mu_j$, and an effective length of a material to be decomposed as $L_j$, following Equation (1) is satisfied. In the conventional technique, an effective length of a material to be decomposed is calculated by establishing Equation (2) that is a system of simultaneous equations using the second projection data of each of the first energy bin E1, the second energy bin E2, the third energy bin E3, the fourth energy bin E4, the fifth energy bin E5, and the sixth energy bin E6 shown in FIG. 2.

$$C(E) = C_0(E) \exp^{-\Sigma_{j=1}^{m} \mu_j(E) L_j} \quad (1)$$

$$\begin{pmatrix} lnC_0(E_1) - lnC(E_1) \\ \vdots \\ lnC_0(E_n) - lnC(E_n) \end{pmatrix} = \begin{pmatrix} \mu_1(E_1) & \cdots & \mu_m(E_1) \\ \vdots & \ddots & \vdots \\ \mu_1(E_n) & \cdots & \mu_m(E_n) \end{pmatrix} \begin{pmatrix} L_1 \\ \vdots \\ L_m \end{pmatrix} \quad (2)$$

Because the subject P in the first embodiment is the phantom PHa, a material to be decomposed, that is a material for which a density distribution is calculated, is the water W, the iodine contrast agent I, and the gadolinium contrast agent G. Therefore, "m=3" is acquired in the first embodiment. As for a subscript j in Equation (1), "j=1" expresses the iodine contrast agent I, "j=2" expresses the gadolinium contrast agent G, and "j=3" expresses the water W.

In the conventional material decomposition, an effective length of a material to be decomposed is calculated by using Equation (2) above, to generate image data of the material to be decomposed. However, the width of the energy bin is narrow and the number of photons is small in the left side of Equation (2), and therefore, influence of a noise is large, and it has been difficult to calculate an effective length of a material to be decomposed accurately only with Equation (2). Therefore, in the present embodiment, Equation (2) is solved under a constraint condition described later, and an effective length of a material is accurately calculated, thereby performing material decomposition with higher accuracy.

The deriving unit 382a derives a constraint condition (step S106). In the first embodiment, the constraint condition includes a first constraint condition and a second constraint condition explained below.

The deriving unit 382a derives the first constraint condition. Specifically, the deriving unit 382a calculates a total transmission length d at each point in projection data that has been used to calculate an effective length, from the CT image im acquired by reconstructing the projection data that has been used to derive a constraint condition. For example, the deriving unit 382a calculates the total transmission length d from information included in one point of the first projection information PJ1, acquires following Equation (3), and forms simultaneous equations with Equation (2) to derive Equation (4). Equation (3) is the first constraint condition. Moreover, Equation (3) is also called a regularization term. The first binarized image B1 is an image that is obtained by dividing the CT image im into the region A1 in which the air A is present and the region O1 in which the air A is not present. Therefore, the deriving unit 382a can calculate a total transmission length. Equation (3) expresses the first constraint condition that length of passage of an X-ray that has been emitted from the X-ray tube 121a and has entered one of the X-ray detection elements included in the X-ray detector 13a in the region O1 in which the air A is not present, that is, a sum of an effective length $L_1$ of the iodine contrast agent I, an effective length $L_2$ of the gadolinium contrast agent G, and an effective length $L_3$ of the water W, and the total transmission length d are equal to each other.

$$d = L_1 + L_2 + L_3 \quad (3)$$

$$\begin{pmatrix} lnC_0(E_1) - lnC(E_1) \\ \vdots \\ lnC_0(E_n) - lnC(E_n) \\ d \end{pmatrix} = \begin{pmatrix} \mu_1(E_1) & \cdots & \mu_m(E_1) \\ \vdots & \ddots & \vdots \\ \mu_1(E_n) & \cdots & \mu_m(E_n) \\ 1 & \cdots & 1 \end{pmatrix} \begin{pmatrix} L_1 \\ \vdots \\ L_m \end{pmatrix} \quad (4)$$

The deriving unit 382a derives the second constraint condition. Specifically, the deriving unit 382a calculates a presence probability p of a material to be decomposed at each point of projection data that has been used to calculate an effective length, from the CT image im acquired by reconstructing the projection data that has been used to derive a constraint condition. For example, the deriving unit 382a calculates the presence probability p of the iodine contrast agent I or the gadolinium contrast agent G from brightness of one point of the second projection information PJ2, and derives following Equation (5). Equation (5) is the second constraint condition. The second binarized image B2 is an image that is obtained by dividing the CT image im into the combined region of the region I2 in which the iodine contrast agent I is present and the region G2 in which the gadolinium contrast agent G is present, and the other region O2. Therefore, the deriving unit 382a cannot calculate the effective length $L_1$ of the iodine contrast agent I and the effective length $L_2$ of the gadolinium contrast agent G. However, the deriving unit 382a can set the minimum value and the maximum value of a sum of the effective length $L_1$ of the iodine contrast agent I and the effective length $L_2$ of the gadolinium contrast agent G based on the presence probability p. Accordingly, the second constraint condition is an inequality as shown in Equation (5). α and β in Equation (5) are coefficients for correction. The coefficient α and the coefficient β may be determined empirically, or logically.

$$\alpha p \leq L_1 + L_2 \leq \beta p \quad (5)$$

The calculating unit 383 calculates an effective length of a material to be decomposed (step S107). Specifically, the calculating unit 383 calculates an effective length by using constraint condition and projection data in which counted values of photons at respective points in at least two pieces of projection data are added up. More specifically, the calculating unit 383 calculates the effective length $L_1$ of the iodine contrast agent I, the effective length $L_2$ of the gadolinium contrast agent G, and the effective length $L_3$ of the water W from Equation (4) derived including the first constraint condition and Equation (5) that is the second constraint condition. Subsequently, the calculating unit 383 determines whether the processing at step S105 to step S107 has been performed for all of points in the first projection data P1 (step S108). When the processing at step S105 to S107 has not been performed for all of the points in the first projection data P1 (step S108: NO), it returns to step S105. When the processing at step S105 to S107 has been performed for all of the points in the first projection data P1 (step S108: YES), it proceeds to step S109.

The generating unit 384 reconstructs an effective length of a material to be decomposed, and calculates information about the material to be decomposed (step S109). Specifically, the calculating unit 383 reconstructs the effective length $L_1$ of the iodine contrast agent I, the effective length $L_2$ of the gadolinium contrast agent G, and the effective length $L_3$ of the water W, to calculate a density distribution of the iodine contrast agent I, a density distribution of the gadolinium contrast agent G, and a density distribution of the water W.

The generating unit 384 generates image data of a material to be decomposed (step S110). For example, the generating unit 384 generates image data to display information about the material to be decomposed based on the projection data that has been used to calculate the effective length and the total transmission length d. Alternatively, the generating unit 384 generates image data to display information about the material to be decomposed based on the projection data that has been used to calculate the effective length and the presence probability p. Specifically, the generating unit 384 generates image data that is data to display the density distribution of the iodine contrast agent I, the density distribution of the gadolinium contrast agent G, and the density distribution of the water W in the CT image im. The image data is output to the display unit 32, and the display unit 32 displays the CT image im and a display image of the iodine contrast agent I, a display image of the gadolinium contrast agent G, and a display image of the water W that are displayed in a superimposed manner thereon. Moreover, for example, the generating unit 384 may allocate respective colors to the display image of the iodine contrast agent I, the display image of the gadolinium contrast agent G, and the display image of the water W. This enables an operator to identify decomposed materials easily.

One example of processing performed by the X-ray CT apparatus 1a according to the first embodiment has been explained above. As described above, the X-ray CT apparatus 1a calculates the effective length $L_1$ of the iodine contrast agent I, the effective length $L_2$ of the gadolinium contrast agent G, and the effective length $L_3$ of the water W by using a calculation formula derived from the second projection data under a constraint condition that is calculated from the first projection data P1, that is, the first constraint condition and the second constraint condition. The effective lengths $L_1$, $L_2$, and $L_3$ calculated by the X-ray CT apparatus 1a are what are acquired by adding up the counted values of photons of these six pieces of the second projection data at respective positions of the respective X-ray detection elements and the X-ray tube 121a, and therefore, are what are calculated under the first constraint condition and the second constraint condition calculated from the first projection data P1 in which the number of photons is large and the influence of a noise is small. Therefore, the X-ray CT apparatus 1 according to the first embodiment can suppress degradation in accuracy of material decomposition due to noises. The constraint condition is preferable to be derived from projection data influence of a noise of which is not maximum. Thus, the X-ray CT apparatus 1a according to the first embodiment calculates an effective length of a material to be decomposed under a constraint condition derived from projection data influence of a noise of which is not maximum. Therefore, it is possible to suppress degradation in accuracy of material decomposition caused by projection data influence of a noise of which is maximum.

Furthermore, the X-ray CT apparatus 1a according to the first embodiment may calculate the effective lengths $L_1$, $L_2$, and $L_3$ by using a calculation formula derived from the second projection data under the first constraint condition and the second constraint condition that are calculated from the first projection data P1, without reconstructing the first projection data P1. Furthermore, the X-ray CT apparatus 1a may calculate the effective lengths $L_1$, $L_2$, and $L_3$ by using a calculation formula that is calculated from the second projection data under the first constraint condition and the second constraint condition that are calculated from the first projection data P1. A range in which all of energy bins corresponding to the second projection data are combined may be set based on a constraint condition.

Moreover, the second projection data may be projection data that is acquired by adding up counted values of photons in a plurality of energy bins at the respective positions of the X-ray tube 121a and the respective X-ray detection elements. For example, the second projection data may be projection data that is acquired by adding up counted values of photons in two to five energy bins out of six energy bins shown in FIG. 2 at the respective positions of the X-ray tube 121a and the respective X-ray detection elements. Furthermore, although the energy bins corresponding to the second projection data partly overlap with the energy bins corresponding to the first projection data in the example described above, the energy bins corresponding to the first projection data and the energy bins corresponding to the second projection data need not overlap with each other at all.

Moreover, for a region in which a material to be decomposed is not present or a region in which the presence probability of a material to be decomposed is low in the first projection data P1, reconstruction is not necessary to be performed. For example, for a region in which the iodine contrast agent I or the gadolinium contrast agent G is not present, or a region in which the presence probability of the iodine contrast agent I or the gadolinium agent G is low, reconstruction is not necessary to be performed. Thus, reconstruction is only necessary to be performed in a part the reconstruction is required, and therefore, the processing load is reduced, and a result of material decomposition can be displayed speedily.

Figure 12:
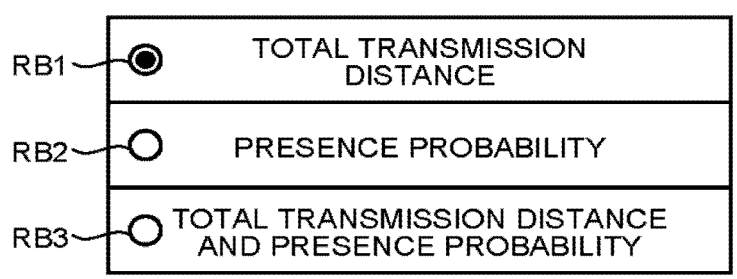
FIG. 12 depicts a selecting screen that is used when a constraint condition is selected.
Figure 13:
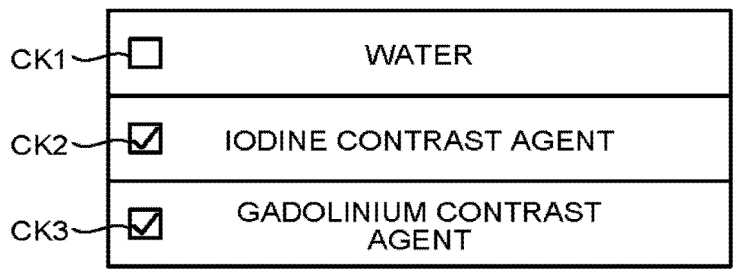
FIG. 13 depicts a selecting screen that is used when a material to be decomposed is selected.

Next, a selecting screen that is presented to an operator at the time of material decomposition is explained referring to FIG. 12 and FIG. 13. FIG. 12 depicts a selecting screen that is presented when a constraint condition is selected. FIG. 13 depicts a selecting screen that is presented when a material to be decomposed is selected.

The display unit 32 may display a selecting screen as shown in FIG. 12 so that an operator of the X-ray CT apparatus 1a can select a constraint condition to be used when an effective length of a material to be decomposed is calculated. The selecting screen shown in FIG. 12 has a radio button RB1 to select only the total transmission length d as a constraint condition, a radio button RB2 to select only the presence probability p of the iodine contrast agent I or the gadolinium contrast agent G as a constraint condition, and a radio button RB3 to select the total transmission length d and the presence probability p of the iodine contrast agent I or the gadolinium contrast agent G as a constraint condition. Thus, an operator can select a constraint condition that is preferable for calculating an effective length of a material to be decomposed, by selecting the radio button RB1, the radio button RB2, or the radio button RB3 included in the selecting screen.

Moreover, the display unit 32 can display a selecting screen as shown in FIG. 13 so that an operator of the X-ray CT apparatus 1a can select a material to be displayed. The selecting screen shown in FIG. 13 has a check box CK1 to display information about the water W on the display unit 32, a check box CK2 to display information about the iodine contrast agent I on the display unit 32, and a check box CB3 to display information about the gadolinium contrast agent G on the display unit 32. Thus, an operator can display only a material that is necessary for diagnosis by choosing at least one of the check box CK1, the check box CK2, and the check box CK3 included in the selecting screen.

Second Embodiment

In the first embodiment, a case in which material decomposition is performed using a constraint condition in the X-ray CT apparatus 1a performing photon-counting CT has been explained. However, the material decomposition using a constraint condition explained in the first embodiment is also applicable in an apparatus that performs imaging with various kinds of tube voltages, and collects projection data of a plurality of energy bins by using ordinary integral detectors. Therefore, in a second embodiment, a case in which the image processing method explained in the first embodiment is applied to a dual-energy CT apparatus that collects projection data of a plurality of energies by using two different kinds of tube voltages is explained.

Figure 14:
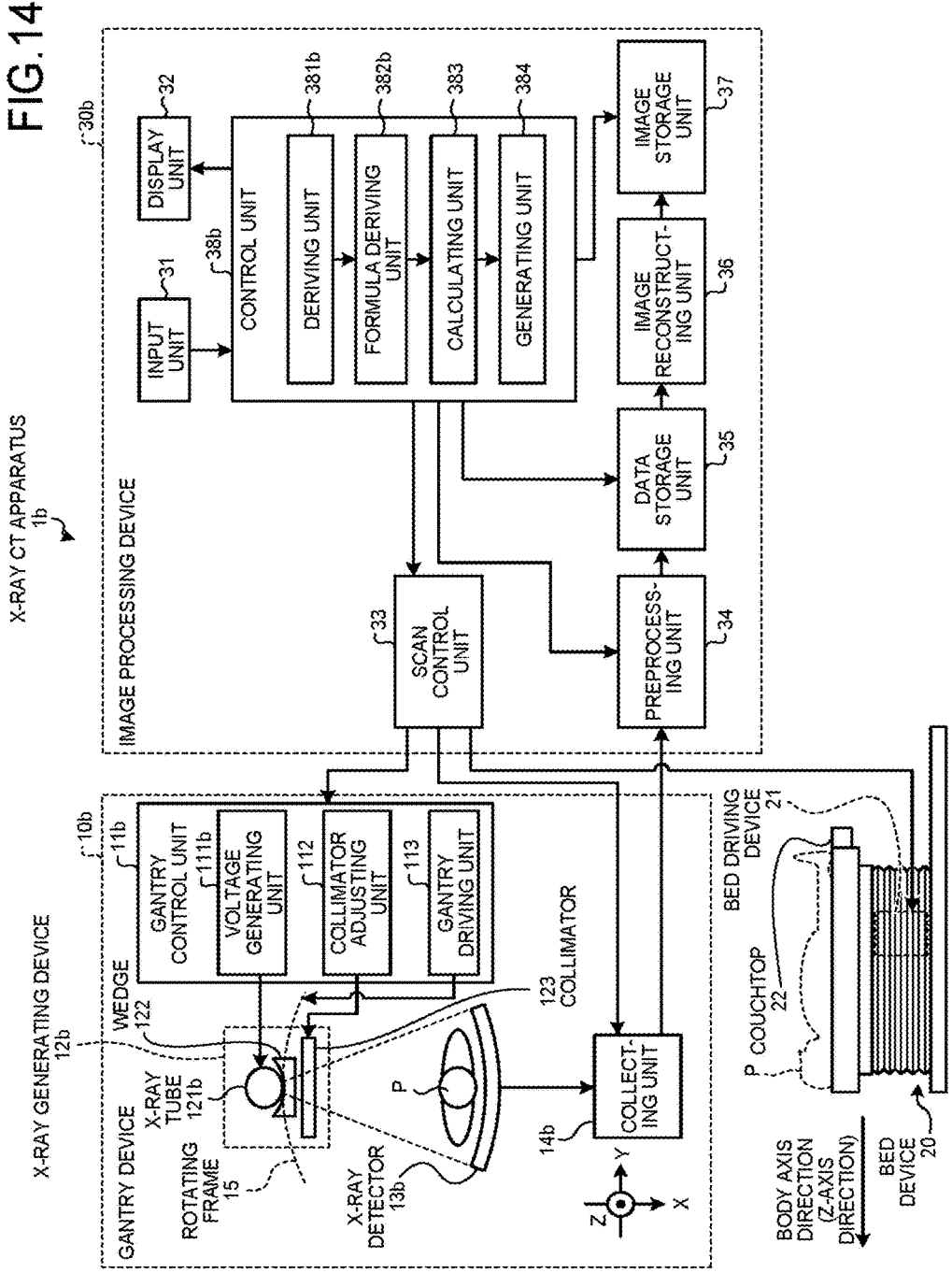
FIG. 14 depicts a configuration of an X-ray CT apparatus according to a second embodiment.

FIG. 14 depicts an X-ray CT apparatus 1b according to the second embodiment. The X-ray CT apparatus 1b includes a gantry device 10b, the bed device 20, and an image processing device 30b as shown in FIG. 14.

The gantry device 10b collects projection data by irradiating an X-ray to the subject P. The gantry device 10b includes a gantry control unit 11b, an X-ray generating device 12b, an X-ray detector 13b, a collecting unit 14b, and the rotating frame 15.

The gantry control unit 11b controls an action of the X-ray generating device 12b and the rotating frame 15 based on control of the scan control unit 33. The gantry control unit 11b includes a voltage generating unit 111b, the collimator adjusting unit 112, and the gantry driving unit 113. The voltage generating unit 111b supplies tube voltages having different values to an X-ray tube 121b. For example, the voltage generating unit 111b supplies two tube voltages having different values to the X-ray tube 121b. Thus, the X-ray tube 121b generates two kinds of X-rays having different energy distributions. Therefore, projection data collected by the collecting unit 14b includes first projection data and second projection data. The first projection data and the second projection data differ in the tube voltage supplied by the X-ray tube 121b.

When the voltage generating unit 111b supplies three or more tube voltages having different values to the X-ray tube 121b, the X-ray tube 121b may irradiate three or more kinds of X-rays having different energy distributions to the subject P.

The X-ray detector 13b is a multi-row detector that includes a plurality of X-ray detection elements that output a signal based on an incident X-ray. The X-ray detection elements are arranged in a channel direction and a slice direction. The X-ray detection element included in the X-ray detector 13b detects the intensity of an X-ray that is generated by the X-ray tube 121b and is irradiated to the subject P. The collecting unit 14b collects a plurality of pieces of projection data by collecting the intensities of a plurality of X-rays that are generated with a plurality of tube voltages and have different energy distributions. For example, the collecting unit 14b collects projection data by an X-ray generated with a first tube voltage (140 kilovolts (kV)) as the first projection data, and collects projection data by an X-ray generated with a second tube voltage (80 kV) as the second projection data. The voltage generating unit 111b supplies three or more kinds of tube voltages having different values to the X-ray tube 121b, and three or more kinds of X-rays having different energy distributions are irradiated to the subject P. In this case, the collecting unit 14b collects the equal number of pieces of projection data to the number of kinds of the applied tube voltages.

The image processing device 30b includes the input unit 31, the display unit 32, the scan control unit 33, a preprocessing unit 34, the data storage unit 35, the image reconstructing unit 36, the image storage unit 37, and a control unit 38b.

The control unit 38b controls the X-ray CT apparatus 1b by controlling actions of the gantry device 10b, the bed device 20, and the image processing device 30b. As shown in FIG. 14, the control unit 38b includes a deriving unit 381b, a formula deriving unit 382b, the calculating unit 383, and the generating unit 384.

The deriving unit 381b derives a constraint condition by using at least two pieces of projection data out of a plurality of pieces of projection data collected by the collecting unit 14b. That is, in the second embodiment, the deriving unit 381b derives a constraint condition by using the first projection data and the second projection data. The formula deriving unit 382b derives a calculation formula to calculate an effective length of a material to be decomposed from the first projection data and the second projection data. Details of the deriving unit 381b and the formula deriving unit 382b are described later.

Figure 15:
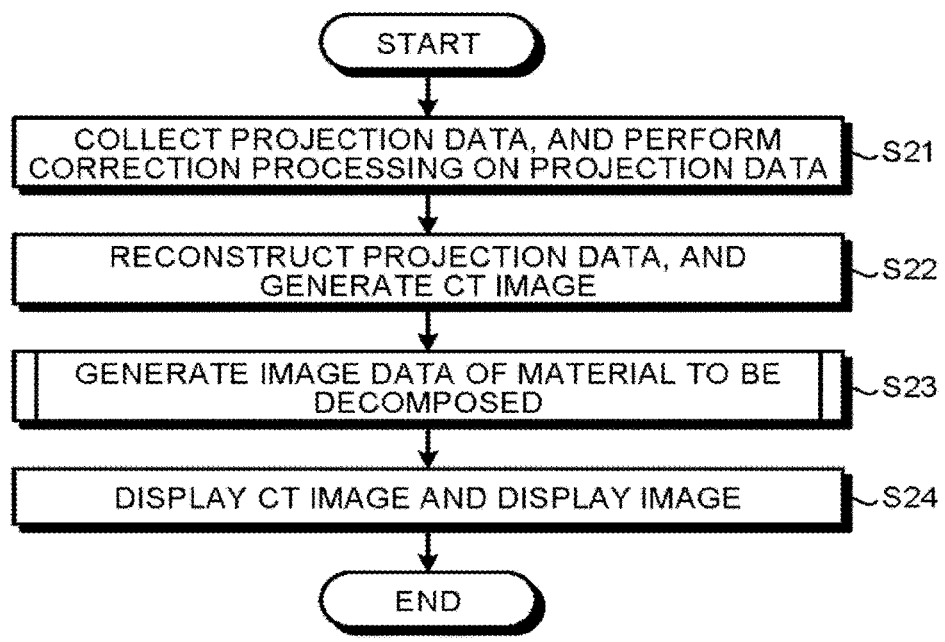
FIG. 15 is a flowchart indicating a procedure of material decomposition that is performed by the X-ray CT apparatus according to the second embodiment.
Figure 16:
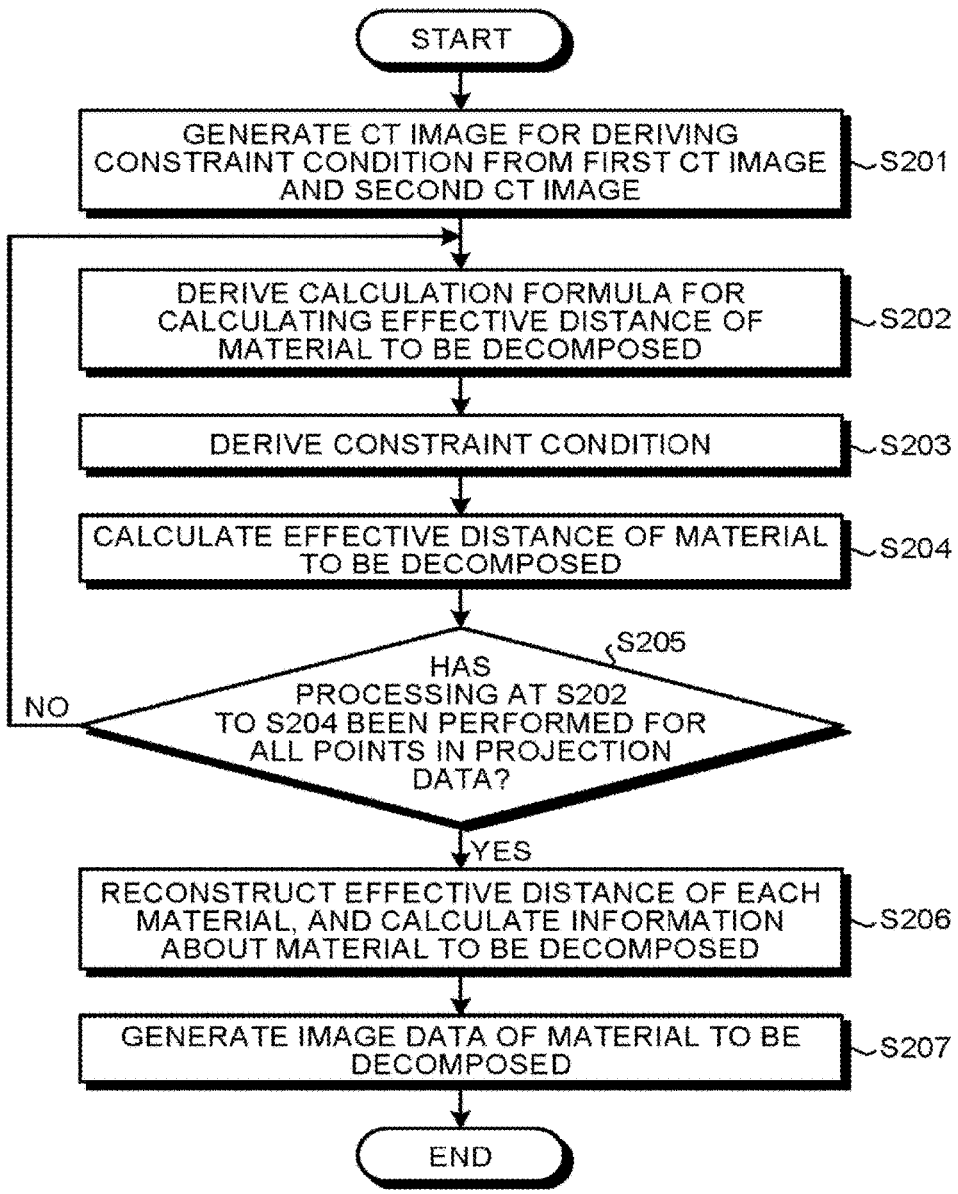
FIG. 16 is a flowchart indicating a procedure of generating image data of a material that is decomposed by the X-ray CT apparatus according to the second embodiment.
Figure 17:
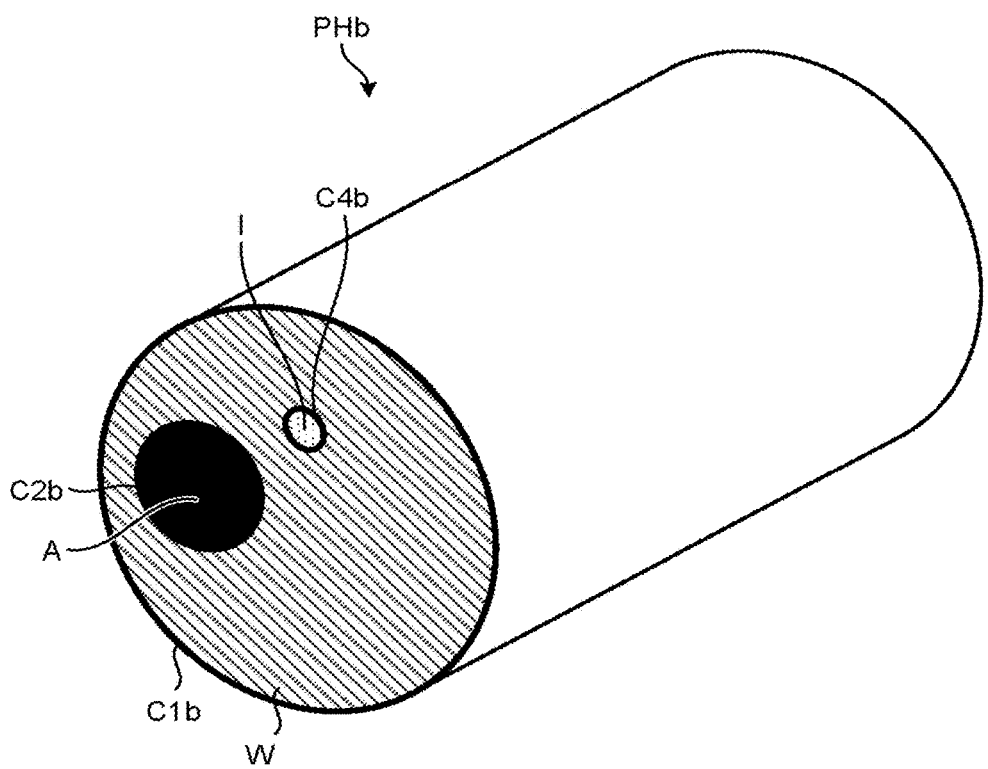
FIG. 17 depicts a phantom for which dual-energy CT imaging is performed by the X-ray CT apparatus according to the second embodiment.

Next, one example of processing performed by the X-ray CT apparatus 1b according to the second embodiment is explained referring to FIG. 15 to FIG. 17. FIG. 15 is a flowchart indicating a procedure of material decomposition that is performed by the X-ray CT apparatus 1b according to the second embodiment. FIG. 16 is a flowchart indicating a procedure of generating image data of a material that is decomposed by the X-ray CT apparatus 1b according to the second embodiment. FIG. 17 depicts a phantom PHb for which dual-energy CT imaging is performed by the X-ray CT apparatus 1b according to the second embodiment.

A case in which dual-energy CT imaging is performed with the phantom PHb shown in FIG. 17 as the subject P is explained as an example. The phantom PHb has a cylinder C1b, a cylinder C2b, and a cylinder C4b center axes of which are parallel to each other, and diameters of bottom surfaces of which are different from each other. The diameter of the cylinder C1b is larger than the diameters of the cylinder C2b, and the cylinder C4b. The cylinder C2b, and the cylinder C4b are included inside the cylinder C1b. The air A is filled inside the cylinder C2b. The iodine contrast agent I is filled inside the cylinder C4b. Water W is filled in a region surrounded by the cylinder C2b, the cylinder C4b, and the cylinder C1b. Moreover, the phantom PHb is arranged in the air.

The control unit 38b controls the gantry device 10b, the bed device 20, and the image processing device 30b to perform dual-energy CT imaging, thereby collecting projection data, and controls the preprocessing unit 34 to perform correction processing on the projection data (step S21). The X-ray CT apparatus 1b performs dual-energy CT imaging by, for example, a dual spin method. The dual spin method is an imaging method in which the first projection data is acquired by rotating the rotating frame 15 once in a state in which the first tube voltage is applied to the X-ray tube 121b, and then the second projection data is acquired by rotating the rotating frame 15 once in a state in which the second tube voltage is applied to the X-ray tube 121b. Because the X-ray CT apparatus 1b is a dual-energy CT apparatus, each point in the projection data includes information about the intensity of an X-ray that has passed through the subject P.

The image reconstructing unit 36 reconstructs projection data stored in the data storage unit 35 to generate a CT image (step S22). Specifically, a first CT image is generated by reconstructing the first projection data, and a second CT image is generated by reconstructing the second projection data. Therefore, the CT image that is generated by the image reconstructing unit 36 includes the first CT image and the second CT image. The control unit 38b performs various kinds of processing on the CT image generated at step S22, that is the first CT image and the second CT image, to generate image data of a material to be decomposed (step S23). The display unit 32 displays the CT image and a display image that shows a density distribution and the like of the material to be decomposed (step S24). For example, on the display unit 32, three images of an image that is obtained by performing addition processing on the first CT image and the second CT image, the first CT image, and the second CT image are displayed, and the display image is superimposed on these images to be displayed. Details of step S23 are as described below.

The deriving unit 381b generates a CT image for deriving a constraint condition from the first CT image and the second CT image (step S201). Specifically, the deriving unit 381b generates the CT image for deriving a constraint condition by averaging the first CT image and the second CT image. Because the CT image for deriving a constraint condition is an image that is obtained by averaging the first CT image and the second CT image, influence of a noise is reduced. The CT image for deriving a constraint condition may be generated by root-mean squaring the first CT image and the second CT image.

The formula deriving unit 382b derives a calculation formula to calculate an effective length of a material to be decomposed (step S202). Specifically, the formula deriving unit 382b derives a calculation formula to calculate an effective length of the material to be decomposed from each of the first projection data and the second projection data. As a calculation formula to calculate an effective length of a material, for example, there is an equation similar to above Equation (2).

The deriving unit 381b derives a constraint condition (step S203). That is, the deriving unit 381b derives a constraint condition by using at least two pieces of projection data out of a plurality of pieces of projection data. A specific method of deriving a constraint condition by the deriving unit 381b is as described below.

For example, the deriving unit 381b derives a constraint condition from the CT image for deriving a constraint condition. As a constraint condition, for example, there are an equation similar to above Equation (3) and an equation similar to Equation (5). Alternatively, the deriving unit 381b may derive a constraint condition from one the influence of a noise of which is not maximum out of the first projection data and the second projection data. For example, as the number of photons increases, the influence of a noise decreases. Accordingly, because as the number of photons increases, the influence of a noise decreases, it is possible to suppress degradation in accuracy of material decomposition due to a noise.

The calculating unit 383 calculates an effective length of a material to be decomposed (step S204). Subsequently, the calculating unit 383 determines whether the processing at step S202 to step S204 has been performed for all of points in projection data (step S205). When the processing at step S202 to step S204 has not been performed for all of the points in the projection data (step S205: NO), it returns to step S202. When the processing at step S202 to step S204 has been performed for all of the points in the projection data (step S205: YES), it proceeds to step S206.

The calculating unit 383 reconstructs an effective length of the material to be decomposed, and calculates information of the material to be decomposed (step S206). Specifically, the calculating unit 383 reconstructs the effective length $L_1$ of the iodine contrast agent I and the effective length $L_3$ of the water W, to calculate a density distribution of the iodine contrast agent I and a density distribution of the water W.

The generating unit 384 generates image data of a material to be decomposed (step S207). Specifically, the generating unit 384 generates image data that is data to display the density distribution of the iodine contrast agent I and the density distribution of the water W in the CT image in a superimposed manner. The image data is transmitted to the display unit 32, and the display unit 32 displays the CT image and a display image of the iodine contrast agent I and a display image of the water W that are displayed in a superimposed manner thereon.

One example of processing performed by the X-ray CT apparatus 1b according to the second embodiment has been explained above. As described above, the X-ray CT apparatus 1b calculates the effective length $L_1$ of the iodine contrast agent I and the effective length $L_3$ of the water W by using a calculation formula derived from the first projection data and the second projection data under a constraint condition that is derived from the CT image for deriving a constraint condition. The effective lengths $L_1$ and $L_3$ are what are calculated under a constraint condition derived from the CT image for deriving a constraint condition in which influence of a noise is reduced. Therefore, the X-ray CT apparatus 1b according to the second embodiment can suppress degradation in accuracy of material decomposition due to a noise. Moreover, the constraint condition is preferable to be derived from projection data influence of a noise of which is not maximum. Thus, the X-ray CT apparatus 1b according to the second embodiment calculates an effective length of a material to be decomposed under a constraint condition derived from projection data influence of a noise of which is not maximum. Therefore, it is possible to suppress degradation in accuracy of material decomposition caused by projection data influence of a noise of which is maximum.

Furthermore, although as the second embodiment, the dual-energy CT imaging by the dual-spin method has been explained as an example, the dual-energy CT imaging is not limited to a particular system. What has been described above is applicable to dual-energy CT imaging in, for example, a high-speed switching method, a two-tube method, a double-layer detector method, and the like. The high-speed switching method is an imaging method in which voltages to be supplied to an X-ray tube are switched at a high speed per view, and high voltage projection data and low voltage projection data are alternately acquired while a rotating frame rotates once. The two-tube method is an imaging method in which an X-ray tube to which a high voltage is supplied and an X-ray tube to which a low voltage is supplied are arranged, and high voltage projection data and low voltage projection data are simultaneously acquired while a rotating frame rotates once. The double-layer detector method is an imaging method in which X-ray detectors are arranged in two layers, and an X-ray with low energy is detected by a detector close to an X-ray tube, and an X-ray with high energy is detected by a detector far from the X-ray tube.

Moreover, the voltage generating unit 111b may supply three or more tube voltages having different values to the X-ray tube 121b, irradiate three or more kinds of X-rays having different energy distributions to the subject P, and rotate the rotating frame 15 three or more times at each imaging position along a body axis direction to perform imaging.

Although the water W, the iodine contrast agent I, and the gadolinium contrast agent G have been explained in the first embodiment, and the water W and the iodine contrast agent I have been explained in the second embodiment as the materials to be decomposed as examples, a material to be decomposed is not limited thereto. For example, as another example of a material to be decomposed, calcium, muscle, and fat can be considered. Furthermore, it may be configured such that a material to be decomposed can be selected by an operator by operating the input unit 31.

While in the first embodiment and the second embodiment, the method of analytically calculating an effective length of a material to be decomposed by using Equation (2) or the like has been explained as an example, a method of calculating an effective length of a material to be decomposed is not particularly limited. For example, an effective length of a material to be decomposed may be calculated by using at least one of the first constraint condition and the second constraint condition, and following Equation (6). Equation (6) indicates that an effective length of such a material to be decomposed that a total sum of squared difference between the number of photons of an X-ray detected by an X-ray detection element and an estimated value of the number of photons of the X-ray detected by the X-ray detection element is minimum.

$$\underset{L_1,\ldots,L_M}{\operatorname{argmin}} \left( \sum_{i=1}^{n} \left( C(E_i) - C_0(E_i) \exp^{-\sum_{j=1}^{m} \mu_j(E_i) L_j} \right)^2 \right) \quad (6)$$

Although a constraint condition is derived from a CT image that is generated by reconstructing projection data in the second embodiment, the reconstruction of projection data is not necessarily a required process. For example, it may be configured such that projection data is binarized, and a total transmission length is derived, as a constraint condition, from brightness at each point in the binarized projection data without performing reconstruction of the projection data.

Finally, an embodiment other than the first embodiment and the second embodiment described above is explained.

Although a case in which an X-ray CT apparatus performs various kinds of processing has been explained in the first embodiment and the second embodiment, embodiments are not limited thereto. For example, an image processing system including an X-ray CT apparatus and an image processing apparatus can perform the various kinds of processing described above. The image processing apparatus includes various kinds of devices such as a workstation, an image storage device (an image server) of a picture archiving and communication system (PACS), a viewer, and an electronic patient-chart system, for example. In this case, for example, the X-ray CT apparatus performs collection of projection data and the like. On the other hand, the image processing apparatus receives the projection data and the like collected by the X-ray CT apparatus from the X-ray CT apparatus or an image server through a network, or accepts the projection data and the like by being input by an operator through a recording medium, or the like, to store in a storage unit. Subsequently, the image processing apparatus can perform various kinds of processing described above on the projection data and the like stored in the storage unit.

The instructions indicated in a processing procedure explained in the embodiments described above can be performed based on a program, which is software. By storing this program in a general-purpose computer in advance, and by reading this program, a similar effect as the effect obtained by the X-ray CT apparatus of the embodiments described above can be obtained. The instructions described in the above embodiments is stored, as a program that can be executed by a computer, in a magnetic disk (a flexible disk, a hard disk, and the like), an optical disk (a compact-disc read-only memory (CD-ROM), a compact disc recordable (CD-R), a compact disk rewritable (CD-RW), a digital-versatile-disk read-only memory (DVD-ROM), a digital-versatile disk recordable (DVD±R), a digital-versatile disk rewritable (DVD±RW), and the like), a semiconductor memory, or a recording medium of a similar kind. As long as a recording medium can be read by a computer or an incorporated system, a storage format can be of any form. If a computer reads the program from this recording medium, and causes a CPU to execute instructions described in the program based on this program, actions similar to those of the X-ray CT apparatus of the embodiments described above can be implemented. Furthermore, when acquiring or reading the program, the computer can acquire or read the program through a network.

A part of various kinds of processing to implement the embodiments described above may be performed by an operating system (OS) running on the computer, database management software, middleware (MW) such as a network, or the like based on the instruction of the program installed in the computer or the incorporated system from the recording medium. Furthermore, the recording medium is not limited to a medium that is independent of the computer or the incorporated system, but includes a recording medium that downloads the program transmitted through a local area network (LAN), the Internet, or the like to store, or temporarily store. Moreover, the recording medium is not limited to one, but a case in which the processing in the embodiments described above is performed from more than one medium is also regarded as the recording medium of the embodiment, and a configuration of the medium may take any configuration.

The computer or the incorporated system in the embodiment is to perform various kinds of processing in the embodiments described above based on the program stored in the recording medium, and can take any configuration of a device constituted of one of a personal computer, a microcomputer, and the like, a system in which a plurality of devices are connected through a network, and the like. Furthermore, the computer in the embodiment is not limited to a personal computer, but includes an arithmetic processing device included in an information processing device, a microcomputer, and the like, and is a generic name of a device or an apparatus that is capable of implementing the functions in the embodiments by the program.

Figure 18:
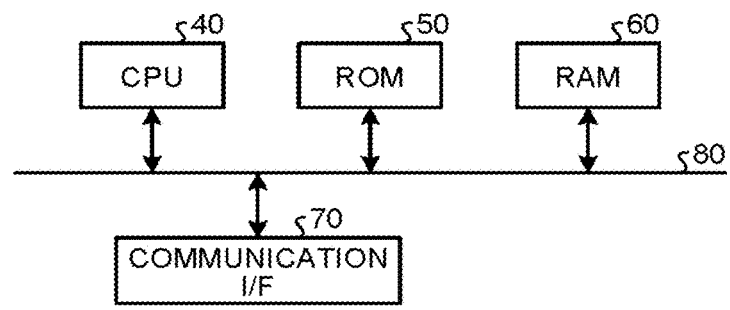
FIG. 18 depicts a hardware configuration of an image processing apparatus according to an embodiment other than the first embodiment and the second embodiment.

FIG. 18 depicts a hardware configuration of the image processing apparatus according to the embodiment other than the first embodiment and the second embodiment. The image processing apparatus of the embodiment described above includes a control device such as a CPU 40, a storage device such as a read-only memory (ROM) 50 and a RAM 60, a communication interface (I/F) 70 that makes communication by connecting to a network, and a bus 80 that connects he respective parts.

A program that is executed by the image processing apparatus according to the embodiment described above is installed in the ROM 50 and the like in advance to be provided. Moreover, the program that is executed in the image processing apparatus according to the embodiment described above can make a computer function as the respective parts of the image processing apparatus described above. In this computer, the CPU 40 can read and execute, on a main storage unit, the program from an image processing method.

Modified Example

Figure 19:
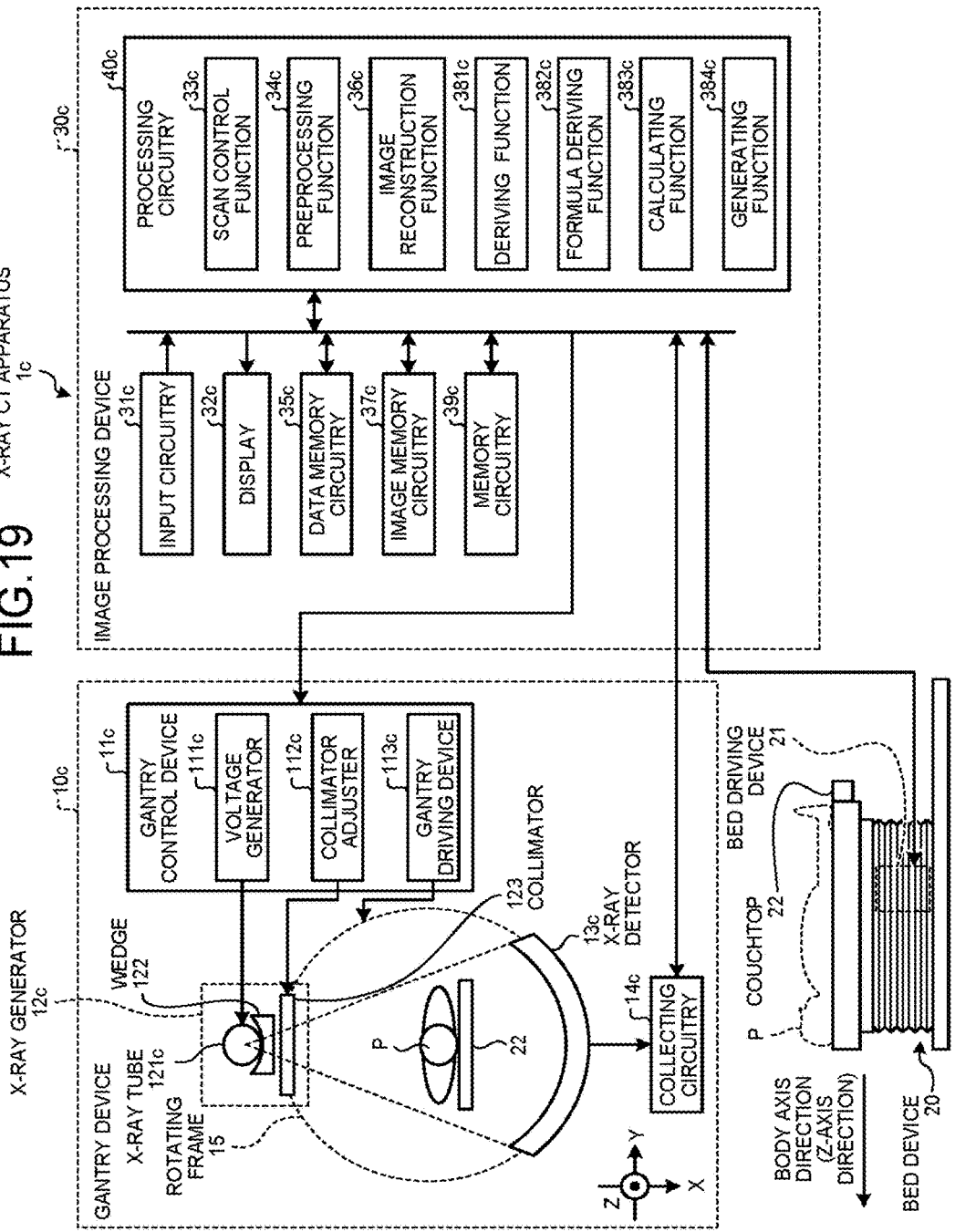
FIG. 19 depicts an X-ray CT apparatus according to the modified example.

With reference to FIG. 19, the following describes a modified example of the embodiment described above. FIG. 19 depicts an X-ray CT apparatus according to the modified example. In regard to the same configurations as those in the embodiments described above, the same reference symbols will be used as those used in the embodiments. With respect to the content that duplicates the embodiment described above, the detailed explanations are omitted. The X-ray CT apparatus 1$c$ includes, as illustrated in FIG. 19, a gantry device 10$c$, the bed device 20, and an image processing device 30$c$.

The gantry device 10$c$ irradiates the subject P with X-rays and collects projection data. The gantry device 10$c$ includes a gantry control device 11$c$, the X-ray generator 12$c$, the X-ray detector 13$c$, collecting circuitry 14$c$, and a rotating frame 15.

The gantry control device 11$c$ includes a voltage generator 111$c$, a collimator adjuster 112$c$, and a gantry drive device 113$c$.

The voltage generator 111$c$ supplies a tube voltage to the X-ray tube 121$c$. The collimator adjuster 112$c$, by adjusting the aperture and position of the collimator 123, adjusts the irradiation range of the X-rays with which the X-ray generator 12$c$ irradiates the subject P. The gantry driving device 113$c$, by rotatively driving the rotating frame 15, rotates the X-ray generator 12$c$ and the X-ray detector 13$c$ in a circular path centered on the subject P.

The gantry driving device 113$c$ includes a motor, an electronic circuit, and a drive mechanism, for example. The motor generates power to rotate the rotating frame 15. The electronic circuit controls the operation of the motor. The drive mechanism transforms the power generated by the motor into the power to rotate the rotating frame 15. The drive mechanism is implemented by the combination of gears, belts, shafts, and bearings, for example.

X-ray generator 12$c$ includes a X-ray tube 121$c$, a wedge 122, and a collimator 123.

The X-ray tube 121$c$ has the same configuration and function as that of the X-ray tube 121$a$ or the X-ray tube 121$b$ that is described in the foregoing embodiments.

X-ray detector 13$c$ has the same configuration and function as that of the X-ray detector 13$a$ or the X-ray detector 13$b$ that is described in the foregoing embodiments.

The collecting circuitry 14$c$ has the same function as that of the collecting unit 14$a$ or the collecting unit 14$b$ that is described in the foregoing embodiments. The collecting circuitry 14$c$ collects the count data described above. Specifically, the collecting circuitry 14$c$ performs such operation by reading out and executing a program stored in memory circuitry 39$c$, which will be described later. The collecting circuitry 14$c$ is implemented by a processor.

The image processing device 30$c$ includes input circuitry 31$c$, a display 32$c$, data memory circuitry 35$c$, image memory circuitry 37$c$, memory circuitry 39$c$, and processing circuitry 40$c$.

The input circuitry 31$c$ is implemented with a mouse and a keyboard used by the user of the photon-counting X-ray CT apparatus 1c to input various instructions and various settings. The input circuitry 31c outputs the various instructions and various settings input by the user as an electrical signal to the processing circuitry 40c described later. The input circuitry 31c has the same function as that of the input unit 31 that is described in the foregoing embodiments. The input circuitry 31c is implemented by the processor.

The display 32c displays, based on the electrical signal received from the processing circuitry 40c described later, the result of a variety of image processing, and GUIs to receive various settings from the user via the input circuitry 31c, for example. The display 32c is a liquid crystal display or an organic electroluminescence (EL) display, for example. The display 32c has the same function as that of the display unit 32 that is described in the foregoing embodiments.

The data memory circuitry 35c stores therein raw data generated by a preprocessing function 34c, which will be described later. The data memory circuitry 35c has the same function as that of the data storage unit 35 that is described in the foregoing embodiments.

The image memory circuitry 37c stores therein CT images generated by an image reconstruction function 36c, which will be described later. The image memory circuitry 37c has the same function as that of the image storage unit 37 that is described in the foregoing embodiments.

The memory circuitry 39c stores therein respective programs to implement a scan control function 33c, the preprocessing function 34c, the image reconstruction function 36c, a deriving function 381c, a formula deriving function 382c, a calculating function 383c, and a generating function 384c. The memory circuitry 39c stores therein a program for the collecting circuitry 14c to implement the function of the data collection unit 14a the data collection unit 14b.

The processing circuitry 40c executes the same function as that of the scan control unit 33 by reading out and executing the program corresponding to the scan control function 33c from the memory circuitry 39c. The processing circuitry 40c executes the same function as that of the preprocessing unit 34 by reading out and executing the program corresponding to the preprocessing function 34c from the memory circuitry 39c. The processing circuitry 40c executes the same function as that of the image reconstruction unit 36 by reading out and executing the program corresponding to the image reconstruction function 36c from the memory circuitry 39c.

The processing circuitry 40c executes the same function as that of the deriving unit 381a or the deriving unit 381b by reading out and executing the program corresponding to the deriving function 381c from the memory circuitry 39c. The processing circuitry 40c executes the same function as that of the formula deriving unit 382a or the formula deriving unit 382b by reading out and executing the program corresponding to the formula deriving function 382c from the memory circuitry 39c. The processing circuitry 40c executes the same function as that of the calculating unit 383 by reading out and executing the program corresponding to the calculating function 383c from the memory circuitry 39c. The processing circuitry 40c executes the same function as that of the generating unit 384 by reading out and executing the program corresponding to the generating function 384c from the memory circuitry 39c. The processing circuitry 40c is implemented by the processor.

The following describes the correspondence of the modified example to the flowcharts illustrated in FIG. 3, FIG. 4, FIG. 15, and FIG. 16.

The processing performed at Step S11 in FIG. 3 is implemented by the processing circuitry 40c reading out and executing the program corresponding to the processing performed by the scan control unit 33 and the preprocessing unit 34 from the memory circuitry 39c. The processing performed at Step S12 in FIG. 3 is implemented by the processing circuitry 40c reading out and executing the program corresponding to the image reconstructing unit 36 from the memory circuitry 39c. The processing performed at Step S13 in FIG. 3 is implemented by the processing circuitry 40c reading out and executing the program corresponding to the deriving unit 381a, the formula deriving unit 382a, the calculating unit 383, and the generating unit 384 from the memory circuitry 39c. The processing performed at Step S14 in FIG. 3 is implemented by the display 32c.

The processing performed at Step S101 to Step S104 in FIG. 4 is implemented by the processing circuitry 40c reading out and executing the program corresponding to the deriving unit 381a from the memory circuitry 39c. The processing performed at Step S105 and Step S106 in FIG. 4 is implemented by the processing circuitry 40c reading out and executing the program corresponding to the formula deriving unit 382a from the memory circuitry 39c. The processing performed at Step S107 and Step S108 in FIG. 4 is implemented by the processing circuitry 40c reading out and executing the program corresponding to the calculating unit 383 from the memory circuitry 39c. The processing performed at Step S109 and Step S110 in FIG. 4 is implemented by the processing circuitry 40c reading out and executing the program corresponding to the generating unit 384 from the memory circuitry 39c.

The processing performed at Step S21 in FIG. 15 is implemented by the processing circuitry 40c reading out and executing the program corresponding to the processing performed by the scan control unit 33 and the preprocessing unit 34 from the memory circuitry 39c. The processing performed at Step S22 in FIG. 15 is implemented by the processing circuitry 40c reading out and executing the program corresponding to the image reconstructing unit 36 from the memory circuitry 39c. The processing performed at Step S23 in FIG. 15 is implemented by the processing circuitry 40c reading out and executing the program corresponding to the deriving unit 381b, the formula deriving unit 382b, the calculating unit 383, and the generating unit 384 from the memory circuitry 39c. The processing performed at Step S24 in FIG. 15 is implemented by the display 32c.

The processing performed at Step S201 in FIG. 16 is implemented by the processing circuitry 40c reading out and executing the program corresponding to the deriving unit 381b from the memory circuitry 39c. The processing performed at Step S202 in FIG. 16 is implemented by the processing circuitry 40c reading out and executing the program corresponding to the formula deriving unit 382b from the memory circuitry 39c. The processing performed at Step S203 in FIG. 16 is implemented by the processing circuitry 40c reading out and executing the program corresponding to the deriving unit 381b from the memory circuitry 39c. The processing performed at Step S204 to Step S206 in FIG. 16 is implemented by the processing circuitry 40c reading out and executing the program corresponding to the calculating unit 383 from the memory circuitry 39c. The processing performed at Step S207 in FIG. 16 is implemented by the processing circuitry 40c reading out and executing the program corresponding to the generating unit 384 from the memory circuitry 39c.

The processor described above is a central processing unit (CPU), a graphics processing unit (GPU), an application specific integrated circuit (ASIC), a programmable logic device (PLD), and a field programmable gate array (FPGA), for example. The programmable logic device (PLD) is a simple programmable logic device (SPLD) and a complex programmable logic device (CPLD), for example.

The processor implements its function by reading out and executing the programs stored in the memory circuitry $39c$. In the modified example described above, single processing circuitry $40c$ implements the scan control function $33c$, the preprocessing function $34c$, the image reconstruction function $36c$, the deriving function $381c$, the formula deriving function $382c$, the calculating function $383c$, and the generating function $384c$. However, in the modified example described above, the processing circuitry $40c$ may be configured by combining a plurality of independent processors.

In the modified example described above, each of the scan control function $33c$, the preprocessing function $34c$, the image reconstruction function $36c$, the deriving function $381c$, the formula deriving function $382c$, the calculating function $383c$, and the generating function $384c$ may be implemented by independent processing circuitry. In the modified example described above, the respective independent processing circuitry that implement the scan control function $33c$, the preprocessing function $34c$, the image reconstruction function $36c$, the deriving function $381c$, the formula deriving function $382c$, the calculating function $383c$, and the generating function $384c$ may be integrated as desired.

Furthermore, the collecting circuitry may be included in the image processing device $30c$.

According to the X-ray CT apparatus and the image processing apparatus of at least one of the embodiments described above, material decomposition can be performed with higher accuracy.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:
1. An X-ray computed-tomography (CT) apparatus, comprising:
    an X-ray tube that generates an X-ray;
    an X-ray detector that includes a plurality of X-ray detection elements configured to output a signal based on the X-ray entered therein; and
    processing circuitry configured to
        derive a constraint condition by using at least one of a plurality of pieces of projection data, each of a plurality of energy bins corresponding to each of the plurality of pieces of projection data, the energy bins differing at least partially, the constraint condition being a condition regarding a sum of a plurality of effective lengths, each of the plurality of effective lengths corresponding to each of a plurality of materials,
        calculate at least one of the plurality of effective lengths by using the plurality of pieces of projection data and the constraint condition, and
        generate image data showing information about at least one of the plurality of materials by using the projection data and the at least one of the plurality of effective lengths.

2. The apparatus according to claim 1, wherein
the processing circuitry is further configured to collect count information that is information in which a position of the X-ray tube, a position of the X-ray detection element to which a photon has entered, an energy of the photon, and a counted value of photons are associated with each other, and collect the plurality of pieces of projection data, the plurality of pieces of projection data being obtained by adding up the counted values of photons of at least two pieces of projection data, at each of a plurality of points in the at least two pieces of projection data.

3. The apparatus according to claim 2, wherein
the processing circuitry is further configured to calculate a total transmission length at each of a plurality of points in the plurality of pieces of projection data to derive the constraint condition, the plurality of pieces of projection data being obtained from a CT image.

4. The apparatus according to claim 2, wherein
the processing circuitry is further configured to calculate a probability of presence of a material to be decomposed at each of a plurality of points in the plurality of pieces of projection data to derive the constraint condition, the plurality of pieces of projection data being obtained from a CT image.

5. The apparatus according to claim 2, further comprising input circuitry configured to select the constraint condition by selecting one of a first constraint condition and a second constraint condition, the first constraint condition being an equation including an effective length of water and a second constraint condition being an inequality regarding a plurality of contrast agents.

6. The apparatus according to claim 1, further comprising:
voltage generating circuitry configured to supply a plurality of different tube voltages to the X-ray tube; and
collecting circuitry configured to collect intensities of a plurality of X-rays that are generated with the plurality of different tube voltages and have different energy distributions to collect the plurality of pieces of the projection data, wherein
the processing circuitry is configured to derive the constraint condition by using at least two pieces of projection data out of the plurality of pieces of projection data collected by the collecting circuitry.

7. The apparatus according to claim 6, wherein
the processing circuitry is further configured to calculate a total transmission length at each of a plurality of points in the plurality of pieces of projection data to derive the constraint condition, the plurality of pieces of projection data being obtained from a CT image.

8. The apparatus according to claim 6, wherein
the processing circuitry is further configured to calculate a probability of presence of a material to be decomposed at each of a plurality of points in the plurality of pieces of projection data.

9. The apparatus according to claim 6, further comprising input circuitry configured to select the constraint condition by selecting one of a first constraint condition and a second constraint condition, the first constraint condition being an equation including an effective length of water and a second constraint condition being an inequality regarding a plurality of contrast agents.

10. The apparatus according to claim 1, wherein
the processing circuitry is thither configured to calculate a total transmission length at each of a plurality of points in the plurality of pieces of projection data to derive the constraint condition, the plurality of pieces of projection data being obtained from a CT image.

11. The apparatus according to claim 1, wherein
the processing circuitry is further configured to calculate a probability of presence of a material to be decomposed at each of a plurality of points in the plurality of pieces of projection data to derive the constraint condition, the plurality of pieces of projection data being obtained from a CT image.

12. The apparatus according to claim 1, further comprising
input circuitry configured to select the constraint condition, by selecting one of a first constraint condition and a second constraint condition, the first constraint condition being an equation including an effective length of water and a second constraint condition being an inequality regarding a plurality of contrast agents.

13. The apparatus according to claim 1, wherein
a range in which all of energy bins corresponding to the plurality of pieces of projection data used to derive the constraint condition by the processing circuitry is larger than a range in which all of energy bins corresponding to the plurality of pieces of projection data used to calculate the effective length by the processing circuitry.

14. The apparatus according to claim 1, wherein
a range in which all of energy bins corresponding to the plurality of pieces of projection data used to calculate the effective length by the processing circuitry is set based on the constraint condition.

15. An image processing apparatus, comprising:
a processor; and
a memory that stores processor-executable instructions that, when executed by the processor, cause the processor to
derive a constraint condition by using at least one of a plurality of pieces of projection data in which energy bins of X-rays corresponding to the plurality of pieces of projection data are different, the constraint condition being a condition regarding a sum of a plurality of effective lengths, each of the plurality of effective lengths corresponding to each of a plurality of materials,
calculate at least one of the plurality of effective lengths by using at least one piece of projection data out of the plurality of pieces of projection data and the constraint condition, and
generate image data showing information about at least one of the plurality of materials from at least one of the effective lengths.

16. An image processing method, comprising:
deriving a constraint condition by using at least one of a plurality of pieces of projection data each of a plurality of energy bins corresponding to each of the plurality of pieces of projection data, the energy bins differing at least partially, the constraint condition being a condition regarding a sum of a plurality of effective lengths, each of the plurality of effective lengths corresponding to each of a plurality of materials;
calculating at least one of the plurality of effective lengths by using the plurality of pieces of projection data and the constraint condition; and
generating image data showing information about at least one of the plurality of materials by using the projection data and the at least one of the plurality of effective lengths.

* * * * *